US006469785B1

(12) United States Patent
Duveneck et al.

(10) Patent No.: US 6,469,785 B1
(45) Date of Patent: *Oct. 22, 2002

(54) OPTICAL DETECTION DEVICE BASED ON SEMI-CONDUCTOR LASER ARRAY

(75) Inventors: Gert Ludwig Duveneck, Bad Krozingen (DE); Karlheinz Gulden, Zürich (CH); Rino Ernst Kunz, Steinmaur (CH); Jürgen Söchtig, Opfikon (CH)

(73) Assignee: Zeptosens AG, Witerswil (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/039,701

(22) Filed: Mar. 16, 1998

Related U.S. Application Data

(63) Continuation-in-part of application No. PCT/EP97/04317, filed on Aug. 8, 1997.

(30) Foreign Application Priority Data

Aug. 16, 1996 (CH) .............................................. 2017/96

(51) Int. Cl.⁷ .............................................. G01N 21/01
(52) U.S. Cl. ...................... 356/244; 356/246; 356/328; 422/82.11; 422/82.05; 385/12
(58) Field of Search ................................ 356/246, 244, 356/344, 317, 326, 318, 328, 417, 128; 250/458.1; 204/451, 452, 455, 470, 601, 603, 605, 619, 612, 620; 372/45, 46, 43, 96; 385/12, 37; 422/82.11, 82.05

(56) References Cited

U.S. PATENT DOCUMENTS

| 4,949,350 A | 8/1990 | Jewell et al. ................. 372/45 |
| 5,073,041 A | 12/1991 | Rastani ........................ 385/33 |
| 5,082,629 A | * 1/1992 | Burgess et al. ............. 356/128 |
| 5,557,627 A | * 9/1996 | Schneider, Jr. et al. ....... 372/45 |
| 5,565,978 A | * 10/1996 | Okubo et al. ............... 356/128 |
| 5,694,215 A | * 12/1997 | Carver ....................... 356/344 |
| 5,867,266 A | * 2/1999 | Craighead ................... 356/344 |

FOREIGN PATENT DOCUMENTS

| DE | 4207431 A1 | 9/1992 |
| EP | 0244394 | 11/1987 |
| EP | 0 445 488 | 9/1991 |
| EP | 0718621 | 6/1996 |
| WO | 91/10122 | 7/1991 |

OTHER PUBLICATIONS

Patent Abstracts of Japan, vol. 018, No. 303 (P–1751), Jun. 9, 1994 & JP 06 066721 A(Yasuhiko Arakawa; Others: 02), Mar. 11, 1994.
Sochtig et al., PSI Yearly Report, May 1997.
Project 1.07, Apr. 9, 1997 (2 sheets).

* cited by examiner

Primary Examiner—Hoa Q. Pham
(74) Attorney, Agent, or Firm—Wenderoth, Lind & Ponack, L.L.P.

(57) ABSTRACT

The invention relates to an optical detection device for chemical analyses, comprising at least one light source, at least one photoelectric detection unit and at least one measuring cell, one or more optical paths coupled to the at least one measuring cell being formed between the light source(s) and the photoelectric detection unit(s). In the course of the miniaturization of such detection devices in arrays for the simultaneous detection of a plurality of analytes, according to the prior art edge-emitting semiconductor lasers that had been separated and applied to a substrate were used. Instead of the latter, the invention provides for surface-emitting semiconductor lasers to be used as light sources, which have the advantage of comparatively simple manufacture and of requiring substantially less space. The process of separating the lasers from the mother substrate and affixing them to a foreign substrate, which was necessary hitherto, is eliminated in the detection device according to the invention.

83 Claims, 9 Drawing Sheets

OPTICAL DETECTION DEVICE BASED ON SEMI-CONDUCTOR LASER ARRAY

This is a continuation-in-part of International Application PCT/EP97/04317, with an international filing date of Aug. 8, 1997.

BACKGROUND OF THE INVENTION

The invention relates to an optical detection device, especially for chemical analyses of small-volume samples, comprising at least one light source for emitting detection light, at least one photoelectric detection unit for detecting a light intensity and converting the light intensity into a corresponding electrical signal, at least one measuring cell for holding a sample to be examined, and one or more optical paths coupled to the at least one measuring cell being formed between the light source(s) and the photoelectric detection unit(s).

It has long been known to carry out qualitative and quantitative chemical analyses of samples by optical means. Examples of such optical measuring methods are electrophoresis and chromatography. In such an optical examination of a sample, detection light emitted by a light source impinges on the sample located in a measuring cell. The light leaving the measuring cell is detected by a photoelectric detection device. When the detection light interacts with the sample, or rather with an analyte contained in the sample, given a suitable absorption spectrum of the analyte, absorption of the detection light can occur and, if the analyte is capable of luminescence, for example as a result of having been suitably prepared with a fluorescence marker, the absorbed detection light can be emitted again by the analyte in the form of luminescence.

For modern biochemical diagnostics there is a general trend towards miniaturization of such optical detection devices so that the use of as small a quantity of sample as possible suffices. Furthermore, in medicine and biochemistry, samples are often examined in respect of several different analytes, so that it is necessary in the course of a rapid processing operation to examine qualitatively, and, where applicable, quantitatively, as far as possible all of the analytes simultaneously.

To examine a sample in respect of various analytes it is known, for example, to bring the sample into contact with a corresponding number of sensor layers, the sensor layers being selectively provided with chemical or biochemical recognition elements immobilized in the sensor layer. The recognition elements each comprise specific affinity partners of the relevant analyte to be detected.

For the optical detection of a specific analyte in the sample it is known, for example, to label the analyte to be detected, which will be captured by the recognition element sensitive thereto which is immobilized on the sensor layer, using a luminescent dye and to detect optically as a measured variable the luminescence radiation or the change in the luminescence radiation of the detection layer resulting from the contact between the analyte and the recognition element.

In the case of optical sensor devices, it is often possible to use the evanescent luminescence excitation method. In that method, excitation light is coupled into a waveguide surrounded by media of lower refractive index. The excitation light is guided in the waveguide by total reflection at the transition between the media having differing refractive indexes. However, in the total reflection, the excitation light enters a short distance into the adjacent medium, with an exponential reduction in its intensity, where it produces the so-called evanescent field. Using the evanescent light intensity, a sample directly adjacent to the optical waveguide can be excited to emit fluorescence. The sensor layer which is provided with the immobilized recognition elements and over which the flowable sample is passed is arranged on the optical waveguide. In such optical sensor devices, the optical waveguide is advantageously in the form of a planar optical waveguide. A planar optical waveguide of that kind on the one hand may be an integral component of a flow cell and serve, for example, as a cover plate for the flow channel and, on the other hand, it can be manufactured simply, and in a manner suitable for mass production, by known deposition methods.

If a large number of analytes is to be examined, it is expedient to arrange the individual biochemical sensor elements in an array. A light source and at least one light detection device are associated in each case with that array of sensor elements. In order to meet the requirements for a small design of the optical detection device, recourse is therefore had to individual edge-emitting semiconductor lasers and conventional semiconductor photodetectors. Such a device comprises, for example, an array of edge-emitting semi conductor lasers mounted on the surface of a substrate, the emission light of which is coupled into respective associated waveguides. The waveguides, which form the interaction zone with the sample, are in contact with the sensor layers provided with recognition elements specific for the relevant analytes. After passing along the interaction zone, the light can be guided via coupling-out devices onto the detection surface of respectively associated semiconductor photodetectors.

The edge-emitting semiconductor lasers are not as a rule, however, produced on the same substrate as the semiconductor photodetectors. Since edge-emitting semiconductor lasers according to conventional production technology emit light parallel to the surface of the substrate, it is necessary either to expose a side edge of a laser element inside the substrate, for example by etching a trench, and guide the emitted light out of the depths of the substrate via deflectors, or to remove the laser unit from the substrate. Since the deflectors in question can be produced only with great difficulty, edge-emitting semiconductor laser elements are usually removed from the substrate and mounted in the desired emission direction on the foreign substrate containing the semiconductor photodetectors. Despite these considerable limitations resulting from the high number of, in some cases, non-automatable operations in the manufacturing of such detector arrangements, in comparison with other laser systems, such as helium-neon lasers, edge-emitting lasers are unrivalled in terms of the space they require and also in their efficiency in converting electrical energy into optical energy, which, in the case of edge-emitting semiconductor lasers, is considerably greater than that of, for example, a helium-neon laser.

However, those known devices have the disadvantage, that there are limits to the increasing miniaturization, inasmuch as, even using edge-emitting semiconductor lasers that have been separated from their mother substrate and applied to a foreign substrate, the surface area occupied by an edge-emitting semiconductor laser is typically 300×100 $\mu m_2$. Owing to the need to separate the edge-emitting semiconductor laser from the mother substrate a and fasten it in a suitable orientation to a foreign substrate, the manufacturing process for an optical detection device according to the difficult and time-consuming and requires manual work, which adds considerably to the costs of the optical detection device.

The purpose of the invention, therefore, is to provide an optical detection device, especially for chemical multiple analyses, preferably of small-volume samples, that has a reduced minimum overall size and a simplified manufacturing process.

That problem is solved according to the invention in a first solution by an optical detection device of the kind previously mentioned that is further distinguished by the fact that each light source is a surface-emitting semiconductor laser.

The surface-emitting laser of the optical detection device according to the invention has, for example in current designs, a size of approximately 10×10 $\mu$m on the substrate, with the result that the surface area occupied can thereby be reduced by a factor of about 1:300 in comparison with a customary commercially semiconductor laser of the kind previously mentioned at the beginning. Furthermore, a surface-emitting laser has a lower power consumption since the threshold currents in that component are lower by about an order of magnitude than in conventional edge-emitting laser diodes. Especially in the case of an array of a large number of detection devices according to the invention on a single substrate, this leads to appreciable easing of the requirement to cool the laser elements.

Compared with the known edge-emitting laser, the surface-emitting laser has the advantage in an optical detection device that, owing to the symmetrical and Gaussian beam profile of the surface-emitting laser, improved beam control and utilization are possible in the down-stream optical elements. Whereas edge-emitting semiconductor lasers generally have an elliptical beam geometry with various and relatively high divergences in the region of up to 30°, the surface-emitting semiconductor laser offers a considerably improved beam quality with a very small divergence of only about 5° half-angle, so that smaller and simpler optical elements can be used.

The surface-emitting semiconductor lasers can be deposited in the form of process- and product-matched stacks of layers of differing stoichiometry in a simple and inexpensive manner by means of known production processes using molecular beam epitaxy or metallo-organic vapour-phase epitaxy methods. Circuits for driving the surface-emitting lasers, other electrical components and also the photoelectric detectors can furthermore be produced on the same substrate. This eliminates the previous is complicated and time-consuming operations of separating, aligning and applying the edge-emitting semiconductor lasers in the chosen array geometry to a foreign substrate which had to be carried out by hand. Rather, the use of surface-emitting semiconductor lasers makes it possible to adopt the technology for the production of integrated circuits which has matured to a high precision. Finally, the surface-emitting semiconductor lasers also have the further advantage of wavelength tuning as a function of their drive current, without longitudinal mode jumps occurring.

In a preferred embodiment of the invention, a plurality of surface-emitting semiconductor lasers is provided on a common substrate. As a result, recourse can be had to the extremely precise methods used in the manufacture of integrated semiconductor circuits for aligning the individual light sources with one another. In particular, the surface-emitting semiconductor lasers have a surface area of approximately 100 $\mu m_2$ on the substrate, so that a massive increase in the packing density of the light sources on the substrate by a factor of approximately 1:300 is possible compared with arrangements having edge-emitting lasers. This enables the optical detection device to be miniaturized, on the one hand, while also enabling a greater number of analytes to be investigated simultaneously.

It is also especially advantageous within the scope of the present invention to design the surface-emitting semiconductor lasers to be suitable for emission of visible light since, as a result, in addition to absorption measurements, the field of fluorescence analysis will also be accessible. Owing to the ability of the surface-emitting semiconductor lasers to be tuned as a function of the drive current, absorption and fluorescence spectroscopy is possible over a wavelength range of several nanometers. Owing to the short resonator length of the surface-emitting semiconductor laser, jumps in the longitudinal mode of the emitted laser light are eliminated, in contrast to conventional, edge-emitting laser diodes, thereby substantially increasing the reliability of the scanning of the accessible wavelength range.

In an especially advantageous manner, in the optical detection device according to the invention, the surface-emitting semiconductor laser is constructed in such a manner that, in the Bragg mirrors of the surface-emitting semiconductor laser, the concentration of the stoichiometric composition of adjacent layers of the multi-layer structure varies in a continuous, especially linear, manner. As a result of that linear graduation of the concentration transitions between the layers, which is also called "grading", the electrical resistance loss of the surface-emitting semiconductor laser for the drive current is reduced. Therefore, a lower power loss being converted into heat occurs, with the result that it is possible, on the one hand, to obtain a higher conversion ratio of electrical power into light power and, on the other hand, to reduce the hitherto-known problem of the substrate becoming heated when several surface-emitting semiconductor lasers integrated on the same substrate are operated simultaneously.

It is also advantageous in the optical detection device according to the invention for the surface-emitting semiconductor laser on the substrate to be defined in its lateral dimension by mesa etching, especially the surface and the flanks of the mesa-etched surface-emitting semiconductor laser being covered by a metal layer, leaving an emission window free for the light emission which is oriented perpendicularly to the substrate surface. This metal layer, which at the same time serves as a metal connection to the surface-emitting semiconductor laser to supply the drive current, causes, by extending over the entire mesa structure, improved heat removal, so that the surface-emitting semiconductor laser can be operated at higher drive currents and hence, a higher maximum light output power can be obtained.

The above-mentioned problem underlying the present invention is solved according to the invention in a second solution by an optical detection device, especially for chemical analyses of small-volume samples, comprising a plurality of light sources for emitting detection light, a corresponding plurality of photoelectric detection units, each associated with a corresponding light source, for detecting a light intensity and converting the light intensity into a corresponding electrical signal, and at least one measuring cell for holding a sample to be investigated, optical paths each interacting with the at least one measuring cell being formed between the light sources and the corresponding photoelectric detection units, wherein the plurality of light sources comprises at least one linear arrangement of edge-emitting semiconductor lasers produced on a common substrate. This second solution according to the invention has the advantage that the semiconductor lasers are produced and installed in the optical detection device in the form of line arrays, whereby the individual semiconductor laser elements within the line are aligned with one another very exactly by virtue of the photolithographic production processes Furthermore, the laborious separation and separate mounting of individual semiconductor elements on a foreign substrate which was customary according to the prior art is considerably simplified and rationalized in this second solution according to the invention, since the edge-emitting semiconductor lasers are formed in lines as one-piece elements comprising 100 or more integrated edge-emitting lasers in a single separating step.

It is also advantageous for the semiconductor laser(s), the photoelectric detection unit(s) and the optical path(s) coupled to the at least one measuring cell to be respectively provided on a first, second and third substrate which is in each case substantially planar. In particular, the first, second and third substrate can be stacked on top of one another. That stacked structure makes possible a modular construction of the optical detection device, with simple and precise alignment of the light sources, the photoelectric detection units and the measuring cells with one another. Owing to this modular construction it is possible to replace the measuring cells from one measurement to the next with a set of fresh measuring cells in a simple manner and without difficulty when the recognition substance immobilized on the sensor layers of the measuring cells has been consumed by a measuring process. It is thereby possible also to achieve cost savings in the measuring process, since the light source arrangement and the arrangement of optical photodetectors are reusable, and assembly of the optical detection device according to the invention is possible in everyday practice without great effort and, as a rule, without the need for special procedures. The various substrates advantageously have registration structures or marks produced by auto-aligning processes. The auto aligning processes comprise, for example, using identical masks in a lithographic process for production of the registration structures or marks.

In another advantageous embodiment, each optical path comprises a waveguide coupled to the at least one measuring cell. The waveguide coupled to the measuring cell is advantageously a monomodal waveguide or a waveguide carrying only few modes and/or a waveguide having a very high refractive index produced, for example, by metal oxides, especially titanium dioxide and tantalum pentoxide. To form a chemical sensor, a chemical coating is applied to the waveguide. Waveguides that are monomodal or that carry only few modes are distinguished by an especially high degree of sensitivity while being as small as possible. That degree of sensitivity is not as a rule achieved by multimode waveguides of planar construction.

Advantageously, at least two planar, separate, preferably inorganic, dielectric waveguides are constructed on a common carrier material to form a sensor platform. A sensor platform of this kind, which is ideally suited for use with an integrated or hybrid semiconductor laser and photodetector array, makes possible a parallel evanescent excitation and detection of the luminescence of identical or different analytes. The separate waveguides may each contain one or more coupling gratings.

A considerable advantage of the sensor platform is that, for example, several sample solutions can be analyzed simultaneously with a high degree of sensitivity. No washing or cleaning steps between individual measurements are required, with the result this a high sample throughput per unit of time is achieved. This is of great significance especially for routine analysis or in the field of genetic engineering analysis.

In addition to the analysis of several sample solutions simultaneously, it is also possible for one sample solution to be examined for several of its analytes simultaneously or in succession on one such sensor platform. This is advantageous especially in the case of blood or serum testing which can thus be carried out especially quickly and economically. When several sample solutions are analyzed simultaneously, the separate waveguides prevent cross-talk between luminescence signals from different samples. A high degree of selectivity and low error rates are achieved with this method. The sensor platform further has an advantage in the fact that the individual separate waveguides can be selectively addressed optically, chemically or fluidically.

Other advantageous embodiments will become apparent.

BRIEF DESCRIPTION OF THE DRAWINGS

The invention is explained and described in detail below by means of preferred embodiments and with reference to the accompanying drawings, in which.

DETAILED DESCRIPTION OF THE INVENTION

Figure 1:
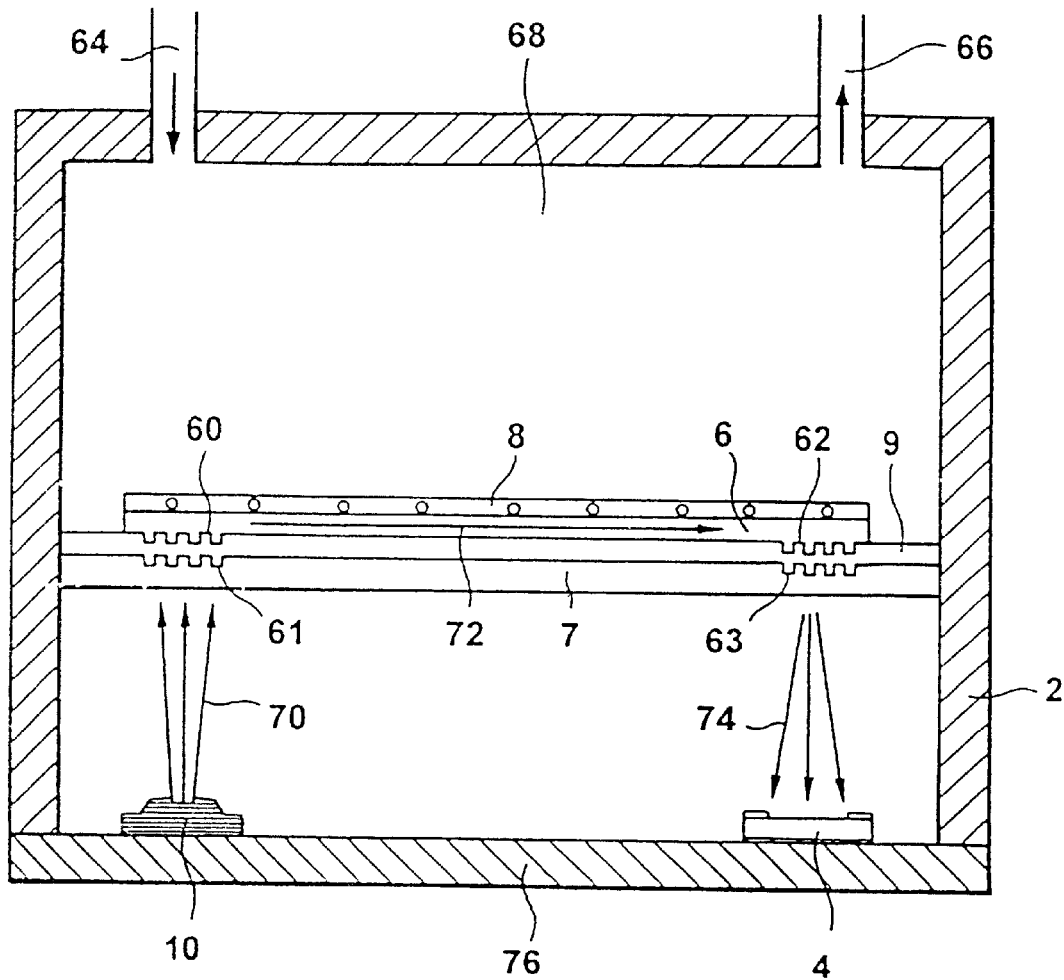
FIG. 1 is a cross-sectional view of a general, first embodiment of the detection device according to the invention.

In FIG. 1, a cross-sectional view of a first embodiment is shown in which the general principle of a detection device according to the invention is illustrated.

In a housing 2, a photoelectric detection unit 4, for example in the form of a photodiode known per se, and a surface-emitting semiconductor laser 10 serving as a light source are mounted on a carrier 76 which may be a component part of the housing. Lying opposite the photodiode 4 and the surface-emitting semiconductor laser 10 is a waveguide 6 which is provided in the housing 2 and the surface of which that faces away from the photodiode and the surface-emitting laser is provided with a sensor layer 8. The waveguide 6 is provided on a substrate 7 which at the same time may constitute a partition wall inside the housing 2, thereby forming inside the housing a chamber 68 that serves as the sample volume. Between the waveguide 6 and the substrate 7 an intermediate layer 9 may be provided which serves, for example, as an adhesion-promoting layer for improving the adhesion, of a waveguide consisting, for example, of metal oxide to an organic substrate. However, the intermediate layer may also act as a separating layer for separating the waveguide from the substrate in order to prevent excitation of parasitic fluorescence in the evanescent field of the waveguide (especially in the case of a substrate consisting of plastics material). A special adhesion-promoting layer (not shown in FIG. 1) may furthermore be provided between the waveguide and the sensor layer.

Leading into the measuring chamber 68 are an inlet channel 64 and an outlet channel 66 through which the fluid samples to be examined can be circulated through the measuring chamber 68 and past the sensor layer 8. The sensor layer 8 may be provided with recognition elements immobilized on the sensor layer which interact with a specific analyte to be detected in the sample, for example by binding to the analyte.

The housing 2 defines a measuring cell to which the waveguide 8 is coupled by the evanescent field of the excitation light propagating through the waveguide. Another possibility for forming an optical path coupled to this measuring cell consists of volume detection when the light emission and light detection devices lie opposite each other on opposite sides of the measuring cell. In that case, a waveguide coupled to the measuring cell would not be necessary. (Quasi) volume detection would also be possible with the use of a waveguide, on the other hand, if the entire luminescence radiation generated in the evanescent field of the waveguide and radiated isotropically were detected by the photodetectors. In this case, a filter would have to be provided over the photodetectors to filter out scattered excitation radiation.

The sample to be examined can either be brought into stationary contact with the sensor layer provided on the waveguide or passed continuously over the waveguide, it being possible for the circulation to be open or closed.

At a position opposite the surface-emitting semiconductor laser, the waveguide 6 has a coupling-in grating 60 which bends radiation 70 emitted by the surface-emitting semiconductor laser in order to couple it into the waveguide 6 so that, in a preferred manner, only one or few modes 72 propagate in the waveguide. The light propagating in the waveguide preferably has a divergence of less than 5°.

At a position opposite the photodiode 4, by a coupling-out grating 62, the light is coupled out of the waveguide and bent into a direction extending substantially perpendicular to the surface of the waveguide 6. A coupled-out beam 74 is then received by the photodiode 4.

The coupling-in grating 60 and the coupling-out grating 62 may be manufactured in any desired conventional manner, for example by processes known to the person skilled in the art, such as scribing, etching or stamping into the substrate 7 gratings 61 and 63 which are transferred conformally via the intermediate layer 9 to the waveguide. The mounting and manufacturing of the sensor layer 8 is also familiar to the person skilled in the art.

In the simplest case, the waveguide could consist merely of a glass plate that at the same time assumes the role of the substrate.

The measuring method of the device shown by way of example in FIG. 1 relies on the interaction of the evanescent light intensity with the sensor layer 8.

The actual measurement can be carried out by radiating in the excitation light continuously, in continuous-wave (cw) operation, that is to say preferably with excitation at a light intensity that is constant with time. Alternatively, however, the measurement can be carried out by radiating in the excitation light in the form of timed pulses having a pulse duration of, for example, from one picosecond to 100 seconds, with which the luminescence can be detected in a time-resolved manner (in the case of a short pulse duration) or at intervals of from seconds to minutes. This method is especially advantageous when, for example, the rate of bond formation is to be followed analytically or a decrease in the luminescence signal as a result of photochemical fading is to be prevented by means of short exposure times. Furthermore, if an appropriately short pulse duration and a suitable time resolution of the detection are used, it is possible to discriminate scattered light, Raman emission and short-lived luminescence of undesired luminescent constituents possibly present in the sample and the sensor material from luminescence of the labelling molecule, which is in this case as long-lived as possible, by detecting the emission of the analyte only after the short-lived radiation has decayed. In addition, as with modulated excitation detection, time-resolved luminescence detection after pulsed excitation allows investigation of the influence of the binding of the analyte on the molecular luminescence decay behaviour. Then molecular luminescence decay time can be used, alongside specific analyte recognition by the immobilized recognition elements and the physical limitation of the signal generation to the evanescent field of the waveguide, as a further selectivity criterion. The excitation light can also be intensity-modulated at one or more frequencies, in which case the resulting phase shift and modulation of the luminescence of the sample is detected.

The device according to the invention is also suitable for the selective, quantitative determination of luminescent constituents in optically opaque fluids. Optically opaque fluids may, for example, be biological fluids, such as egg yolk, body fluids, such as blood, serum or plasma, or also environmental analysis samples, such as surface water, dissolved soil extracts or dissolved plant extracts. Also relevant are reaction solutions of the kind obtained, for example, in chemical production, especially dye solutions or reaction solutions of optical brighteners. Also relevant are all kinds of dispersions and preparations of the kind used, for example, in the textile industry, provided they comprise one or more luminescent components. Owing to the reversibility of the affinity complex formation as an equilibrium process, by using suitable flow rates in the throughflow system, the binding or desorption, i.e. dissociation, of bound, luminescence-labelled affinity partners in the evanescent field can be followed in real time. The device according to the invention is therefore suitable for kinetic studies for determining different association or dissociation constants or for displacement assays.

Figure 2:
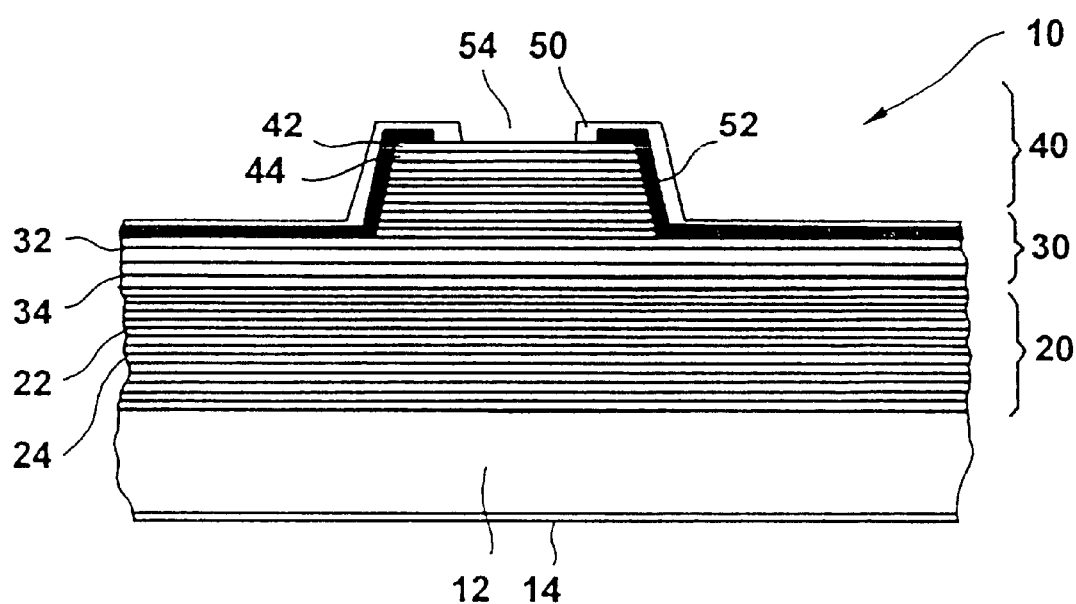
FIG. 2 is a cross-sectional view of a surface-emitting semiconductor laser suitable for use in the present invention.

FIG. 2 shows a cross-section of a surface-emitting semiconductor laser suitable for use in the optical detection device according to the invention. The surface-emitting semiconductor laser is formed on a substrate 12 having a rear-side metal contact 14. The surface-emitting semiconductor laser comprises an active region 30, a rear-side resonator mirror 20 formed from a plurality of layers, and a surface-side resonator mirror 40 likewise formed from a plurality of layers. Provided over the surface of the structure is a metallic contacting layer 50 through which the drive current is conducted. Apart from in a small end region in the vicinity of a laser emission light window 54, an insulating layer formed, for example, from silicon nitride ($Si_3N_4$) lies under the metal layer 50.

For lateral confinement of the drive current entering the stack of layers from the metal layer 50 in the region of the light outlet window 54, which drive current flows to the rear-side electrode 14, a column-like structure is provided at least in the region of the surface-side resonator mirror 40. Instead of that column-like structure, which is also referred to as a mesa structure, it is also possible to carry out a blocking implantation with hydrogen ions in the regions laterally next to the active laser region.

The substrate 12 preferably consists of gallium arsenide n$_+$-implanted with silicon ions. The rear-side mirror is preferably a multilayer interference mirror, also called a Bragg mirror, having, for example, 40 layer sequences of AlAs and $Al_{0.3}Ga_{0.7}As$ which are likewise n-doped. For optimum reflection, each layer has an optical thickness of $\lambda/4$. At an emission wavelength of 765 nm, therefore, the $Al_{0.3}Ga_{0.7}As$ layer has a thickness of 55 nm and the AlAs layer has a thickness of 63 nm. The active region 30 comprises a layer having the thickness of one whole wavelength consisting of $Al_{0.3}Ga_{0.7}As$ in which, preferably in the vicinity of its middle and slightly offset therefrom, three 8 nm thick layers of $Al_{0.12}Ga_{0.88}As$ which are separated by 6 nm wide barriers are provided to form potential wells. The surface-side mirror in turn comprises a stack of layers to form a partially reflecting interference mirror at the emission wavelength of the surface-emitting laser. The surface-side mirror may consist, for example, of 25 layer sequences of $Al_{0.3}Ga_{0.7}As$ and AlAs. At an emission wavelength of 765 nm, the thickness of the AlAs layer is again 63 nm and the thickness of the $Al_{0.3}Ga_{0.7}As$ layer is 55 nm.

The transition in the stoichiometric composition of the mutually adjacent layers of the surface-side and the rear-side Bragg mirror is preferably continuous and, in its simplest and most practical form, has a linear transition. Owing to the continuous linear change in the stoichiometric composition from one layer to the next in the stack of layers of the two Bragg reflectors, the electrical resistance loss for the drive current, which flows perpendicular to the stacks of layers from the metal layer 50 to the rear-side contact 14, is drastically reduced, so that a higher efficiency and a higher optical output power is obtained.

The metal film 50 for supplying the drive current, which is extended over the flanks of the mesa structure, further contributes to creating a high efficiency and high optical light output power. It is advantageous for the mesa structure to be etched back into the substrate as far as possible and for the flanks of the mesa structure to be covered as completely as possible in all directions by the metal film 50. The metal film 50 preferably consists of gold. The fact that the flanks of the mesa structure are covered as completely as possible by the metal film results in optimum removal of the heat in the surface-emitting semiconductor laser, which heat limits the optical output power. A further measure for improving the optical output power of the surface-emitting semiconductor laser comprises confining the current as well as possible in a region vertically below the light outlet window 54, so that all radiative recombination processes take place inside the active region substantially under the light outlet window 54. By that means, radiation losses as a result of absorption in the silicon nitride layer and the metal layer above it are to a large extent avoided. That lateral current confinement can be optimized by mesa etching and additional selective oxidation or selective lateral etching. In the case of such surface-emitting semiconductor lasers, conversion ratios of electrical power into optical power of up to 50% at an emission wavelength of 980 nm can be achieved.

Since the surface-emitting semiconductor laser 10 has a resonator length, which corresponds to the active zone 30, equal to the length of one wavelength, only one longitudinal mode of the laser can be stimulated to oscillate. Furthermore, owing to the circular shaping of the light outlet window 54, the beam profile also is circular and has a Gaussian profile over the cross-section. In addition, the divergence of the laser light emitted from the light outlet window 54 is only about 5° in half-angle. Owing to these properties of the emission light which can be obtained with the surface-emitting semiconductor laser, substantially better beam control and coupling into the waveguide 6 provided with the sensor layer 8 are possible. Furthermore, owing to the small divergence, smaller optical components can be used, which in turn contributes to the possibility of miniaturizing the detector device according to the invention.

A process for the manufacture of the surface-emitting semiconductor laser shown in FIG. 2 is described below. An n$^+$-doped gallium arsenide substrate is provided in an apparatus for molecular beam epitaxy or for metallo-organic vapour-phase epitaxy. On the (100)-surface of the gallium arsenide substrate, the rear-side Bragg mirror is formed from alternating quarter-wavelength layers of AlAs and $Al_{0.3}Ga_{0.7}As$ with 40 layer sequences. Then, in the same operating cycle, an $Al_{0.3}Ga_{0.7}As$ layer having the thickness of one wavelength is formed as the active region, which layer contains three 8 nm thick $Al_{0.12}Ga_{0.88}As$ potential wells separated by 6 nm thick barriers. Still in the same work cycle, the upper, surface-side Bragg mirror having 25 layer sequences, which correspond to the layer sequences of the rear-side Bragg mirror, is then deposited.

The deposition to form the Bragg mirrors is controlled in such a manner that a linear stoichiometric transition in the composition of adjacent layers occurs over a range of 20 nm. During the growth of the stack of layers on the substrate side, silane gas diluted in hydrogen gas is fed in to create n-doping in order to obtain conductivity of the layers. In order, on the other hand, to minimize absorption losses outside the active region, the feeding-in of silane and hence the number of free charge carriers is reduced during growth of the layers at those locations where there is a high optical intensity distribution of the standing wave pattern that occurs during laser operation. The dopant concentration varies in that case approximately between $1 \times 10^{18}/cm^3$ and $2 \times 10^{18}/cm^3$. The surface-side Bragg mirror is p-doped, for example by feeding in bis(cyclopentadienyl)magnesium ($Cp_2Mg$), for example at a concentration of $3 \times 10^{18}/cm^3$, the doping profile also being modulated as in the case of the n-doping. Finally, a thin p$^+$-doped gallium arsenide contact layer is deposited as the uppermost layer.

After the wafer having the deposited stacked layer structure over its entire surface has been removed from the epitaxy apparatus, the rear side of the substrate is coated by vapor deposition with a metal contact, for example consisting of the layer sequence gold, germanium and nickel. After vapor deposition of the rear-side contact, the structure is subjected to an annealing process at 430° C. for 30 seconds. The substrate is then treated using lithographic processes to form one or more discrete surface-emitting laser units. With suitable masking, first dry etching is performed in a reactive ion etcher in a $SiCl_4$ plasma. In that process, mesa etching is carried out, that is to say, leaving a column-shaped region that defines the surface-emitting semiconductor laser, the surrounding substrate is etched back. The dry etching process is interrupted after the uppermost gallium arsenide layer and at least one aluminium arsenide layer have been etched away, whereupon a wet oxidation process or wet etching process is carried out, for example in dilute hydrofluoric acid, with lateral slight etching of the aluminium arsenide layer. By that means, it is possible to obtain a further improvement in the lateral current confinement in the surface-emitting semiconductor laser structure.

The lateral current confinement can additionally be improved by a process using selective layer oxidation, it being possible to provide one or more layers having an increased etch rate in the stack of layers of the surface-side Bragg mirror. For example, for a selective wet oxidation process of the kind, it would be possible to form in the surface-side Bragg mirror a layer sequence of alternating quarter-wavelength layers of $Al_{0.9}Ga_{0.1}As$ and $Al_{0.3}Ga_{0.7}As$, one of the $Al_{0.9}Ga_{0.1}As$ layers being replaced by an AlAs layer in order to create a layer having an increased anisotropic etching behavior. It would thereby be possible to constrict the current path at a location deeper within the surface-side Bragg mirror, which location is determined by the AlAs layer which has an increased anisotropic etching behavior in comparison with the other layers, by etching back that layer, so that an additionally improved current confinement and therewith an increased conversion efficiency is obtained.

The dry etching process is then continued under the initial conditions until an approximately 3.5 μm high laser column with diameters of from 5 to 50 μm is produced. The mesa etching is preferably carried out only in the region of the upper Bragg mirror. For electrical insulation, while masking with a photoresist, an approximately 1 nm thick silicon nitride film is formed on the upper side of the surface-emitting semiconductor laser over the entire wafer by means of plasma-enhanced chemical vapor deposition. Then, the contact windows, which at the same time determine the light outlet windows of the surface-emitting semiconductor laser, are formed by reactive ion etching of the $Si_3N_4$ film in a $CF_4$ plasma. Finally, non-alloyed platinum-titanium-platinum-gold contacts are vapor-deposited, the future laser emission window being masked with photoresist and a contact region existing between the photoresist and the silicon nitride layer on which the contact metal is in contact with the p-doped uppermost gallium arsenide layer. That contact region is annular with a width of about 1–2 μm.

While the upper-side metal contact is being vapor-deposited the substrate is slightly tilted and turned relative to the vapor-deposition source so as to obtain a good covering of the deposited metal on the flanks of the mesa structure for improved heat removal during operation of the surface-emitting semiconductor laser.

By means of known bonding methods a connection is made between the contacts on the upper side and the rear side of the substrate to the appropriate terminals of a suitable drive circuit which may be integrated on another chip. Alternatively, it would be equally possible to integrate the drive circuit on the same chip as that on which the surface emitting semiconductor laser is formed.

The process described above is distinguished by its relative simplicity, thereby making manufacturing simpler and cheaper in comparison with the customary, edge-emitting semiconductor lasers, and hence improving the suitability of the optical detection device according to the invention for mass production. In addition, it also makes it possible to test and characterize the surface-emitting semiconductor laser on the chip before incorporation into the detection device. It is thereby possible for defective or incorrectly manufactured modules to be rejected before the time-consuming and costly procedures for mounting the elements on the carrier for the semiconductor lasers, the wiring thereof and subsequent packaging are carried out.

Figure 3:
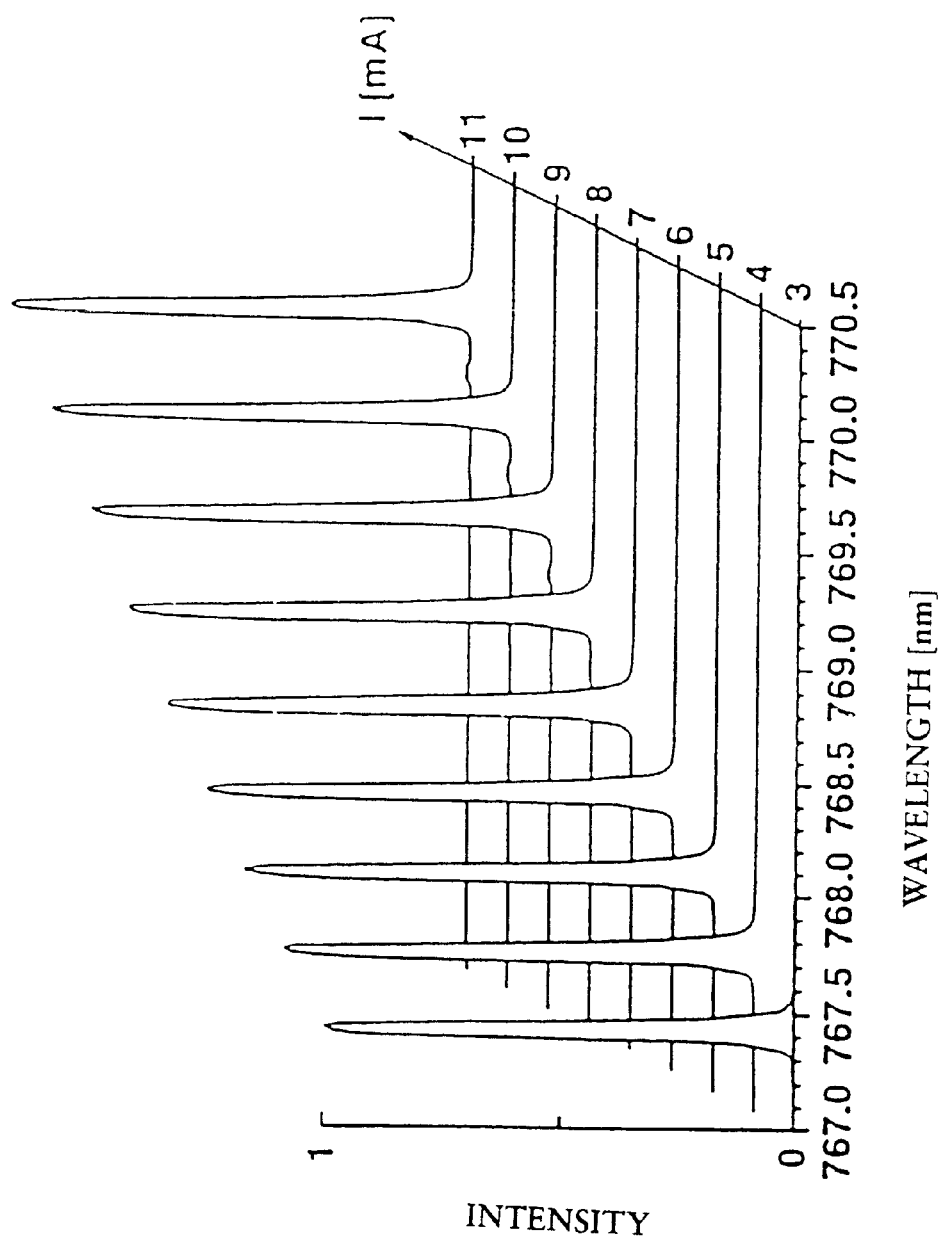
FIG. 3 is a three-dimensional plot of the light emission intensity and the wavelength as a function of the drive current.

In the case of the surface-emitting semiconductor laser 10, it is possible to vary the wavelength of the emission light over a certain wavelength range, for example 2 nm, by varying the drive current of the surface-emitting semiconductor laser. A three-dimensional plot of the emission intensity and the wavelength as a function of the drive current is shown in FIG. 3. The example shown in FIG. 3 relates to a surface-emitting semiconductor laser manufactured by the process described above, which has an emission window of 4 μm radius. In the case of the surface-emitting semiconductor laser, the wavelength increases linearly by 0.31 nm for every increase in the drive current by 1 milliampere. An increase or reduction in the drive current causes a correspondingly increased or reduced power loss, converted into heat, in the surface-emitting semiconductor laser, the optical resonator length being changed by the temperature increase or decrease by way of the corresponding change in the refractive index, thereby making it possible to tune the surface-emitting semiconductor laser over a range of several nanometers.

In the case of the surface-emitting semiconductor laser, it is possible, in contrast to edge-emitting semiconductor lasers, by skillful positioning of the maximum of the gain curve relative to the wavelength of the maximum optical light intensity of the standing wave forming in the active region inside the resonator, to obtain an almost uniform optical output power despite varying the drive current. The maximum light output power is obtained when the maximum gain coincides with the wavelength of the maximum light intensity in the optical resonator. Therefore, the structure can in a skillful manner be made such that, at low drive currents and consequently at a short wavelength of the standing lightwave in the resonator, the gain is at a maximum. Upon increasing the drive current, although, on the one hand, the pump output is increased, on the other hand, owing to the greater wavelength, the intensity maximum of the standing wave drifts away from the maximum of the gain, so that the increase in pump output is compensated for by a deterioration in the gain yield. Since the surface-emitting semiconductor laser is stimulated to oscillate in only a single mode owing to the short resonator length and since the distance to the next longitudinal mode is approximately 100 nm, it is not possible within the relatively narrow-band gain curve of the surface-emitting semiconductor laser for another mode to be stimulated to oscillate and for the optical output power to change suddenly if the wavelength drifts away from the maximum of the gain curve. However, in a conventional, edge-emitting laser, this is possible, since several longitudinal modes can be stimulated to oscillate simultaneously and, upon changing the optical path length inside the resonator, a mode jump will occur, with the result that the emitted wavelength is always matched to the maximum of the gain curve.

Figure 4:
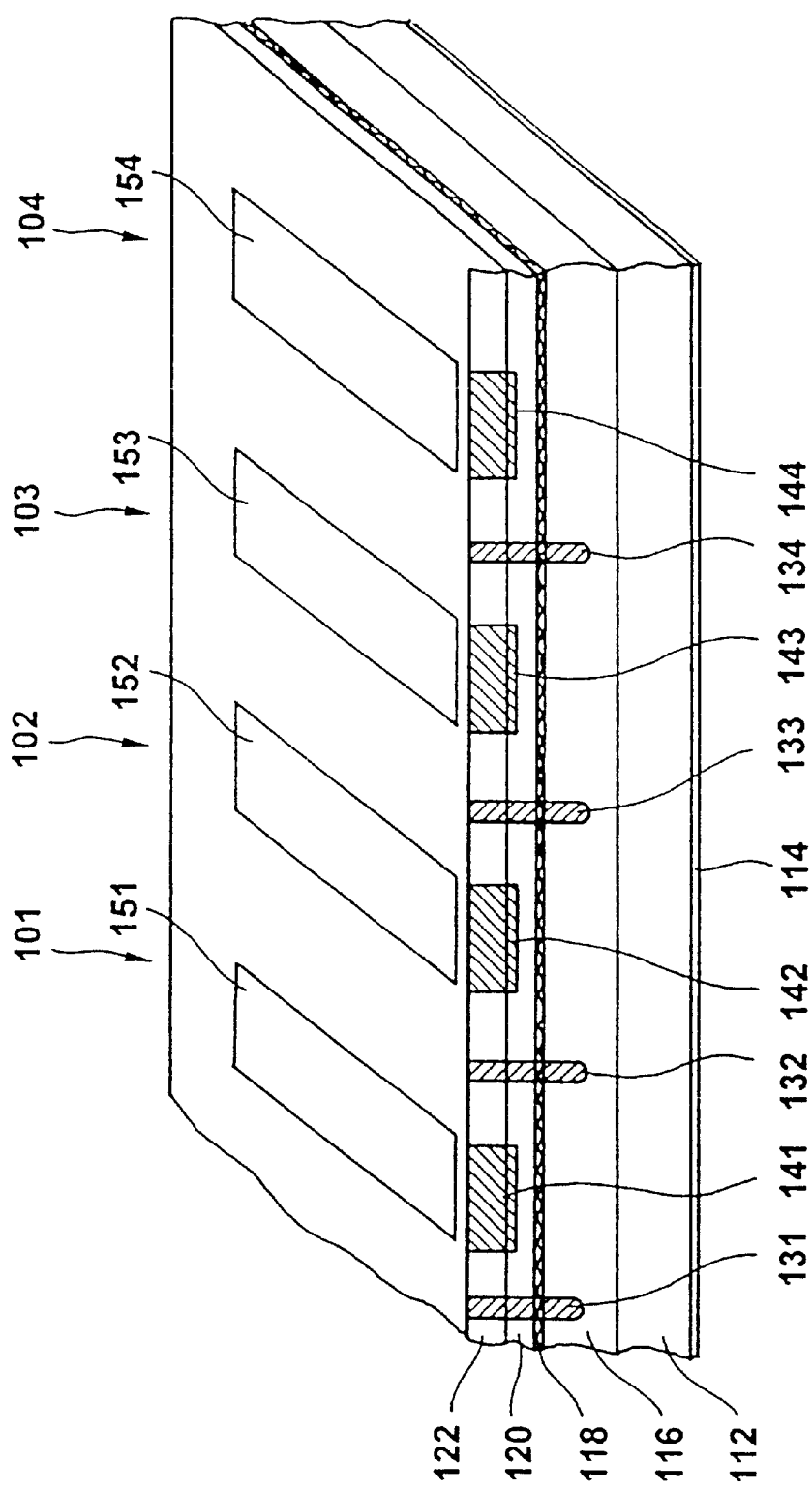
FIG. 4 is a three-dimensional view of a line array according to the invention of edge-emitting lasers.

FIG. 4 shows an embodiment for a linear light source array consisting of a plurality of edge-emitting lasers in accordance with the second solution of the problem of the invention. The linear array of edge-emitting lasers comprises an elongate substrate 112 with a plurality of edge-emitting lasers 101, 102, 103 and 104, which has been broken out of a ready-processed chip as a line having a dimension desired for the subsequent use. The side lying at the front in the three-dimensional view of FIG. 4 has been polished. The embodiment shown in FIG. 4 represents one example for an array of edge-emitting semiconductor lasers, it being obvious to the person skilled in that field of the art that a large number of other structures are possible for the edge-emitting lasers.

In the construction according to FIG. 4, which is shown here merely by way of example, there is applied to the substrate consisting, for example, of n-GaAs a lower cladding 116 consisting of n-AlGaAs over which there is an undoped, active waveguiding layer 118 consisting of GaAs. Over the active waveguiding layer there is an upper cladding 120 consisting of p-AlGaAs over which a cap 122 consisting of p-AlGaAs is provided. For current confinement in the corresponding individual laser structures Zn-diffused regions 141, 142, 143 and 144, for example, are respectively provided under the relevant electrodes 151, 152, 153 and 154, which Zn-diffused regions extend through the cap and into the upper cladding. For electrical isolation to prevent cross-talk between the individual laser diodes, partition implants 131, 132, 133 and 134 are optionally provided between the individual edge-emitting lasers 101, 102, 103 and 104. Instead of using partition implants, it would be possible, for example, to isolate the individual semiconductor lasers by etching. The electrodes 151, 152, 153 and 154 are connected, for example by conventional wire bonding, to a suitable drive circuit. On the rear side of the substrate 112, a contact 114 that is common to all the surface-emitting semiconductor lasers is provided.

Four especially preferred embodiments of the invention will be described below with reference to FIGS. 5, 6, 7 and 8.

Figure 5:
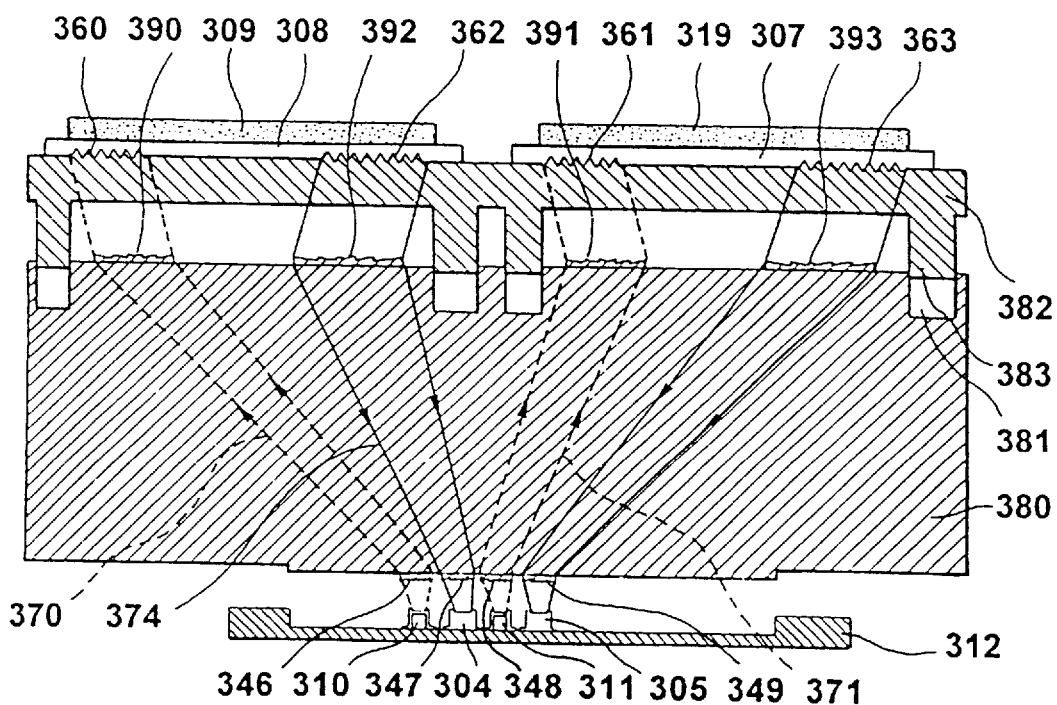
FIG. 5 is a cross-sectional view of a second embodiment of the detection device according to the invention.

FIG. 5 shows a second embodiment of the invention, in which surface-emitting semiconductor lasers 310 and 311 are integrated alongside and alternating with photodetectors 304 and 305 on a common substrate 312. Although, in the embodiment shown in FIG. 5, only two surface-emitting semiconductor lasers and associated photodetectors are shown, the arrangement can, of course, be repeated as often as desired both in the direction of the plane of the drawing and perpendicular to that direction. The size of the array that can, thereby be obtained is essentially limited only by the size of the gallium arsenide substrates available, which at present are commonly in the form of wafers of 2 inches diameter (about 5 cm) for the manufacture of electronic components.

The substrate 312 is constructed to be suitable for mounting on a further substrate 380 in register therewith. For that purpose, the two substrates have, for example, corresponding projections and recesses. Provided on the substrate 380 at the positions opposite the surface-emitting semiconductor lasers are optical beam control elements 346 and 348 which suitably bend the beams emitted by the surface-emitting semiconductor lasers so that they impinge on corresponding beam control components 390 and 391 correspondingly mounted on the other surface of the substrate 380. The corresponding beam control components 390 and 391 bend the beams to corresponding coupling-in gratings 360 and 361 provided on a further substrate 382. The beams coupled into the waveguides 307 and 308 by the coupling-in gratings 360 and 361 propagate with repeated total reflection inside the waveguide to respective coupling-out gratings 362 and 363 through which the light is coupled out and impinges on beam control components 392 and 393 arranged on the sub-strate 380. The latter beam control components 392 and 393 guide the corresponding beams to corresponding beam control components 347 and 349 lying opposite the photodetectors 304 and 305 on the substrate 312.

The flow cell for the fluid passing over the sensor elements 309 and 313 has been omitted in the view shown in FIG. 5.

By means of the beam control components on the two surfaces of the substrate 380 it is possible to obtain a spreading of the beam density from a high density on the side of the array of surface-emitting lasers and photodiodes to a low density on the side of the wave-guide. It is thereby possible, for economical use of the relatively expensive gallium arsenide substrate, to provide a high integration density of the surface-emitting lasers and the associated photodiodes on the gallium arsenide wafer while maintaining relatively large surface areas of the sensors in order to achieve a high degree of sensitivity.

The beam control components on the substrate 380 are preferably in the form of Fresnel lenses, which can be made relatively simply, for example, by stamping processes known to the person skilled in the art. The coupling-in and coupling-out gratings can also be replicated on the substrate 382 in a simple manner by processes known to the person skilled in the art, for example etching or stamping.

The substrate 380 and the substrate 382 on which the coupling-in and coupling-out gratings are provided each have, again, suitable mechanical means 381 and 383 for joining the two substrates together in register. Provided over the waveguide layers 307 and 308 are sensor layers 309 and 319 in each of which a specific recognition element suitable for an analyte to be detected can be immobilized.

The mutual alignment of the substrates 312, 380 and 382 is considerably improved by the use of so-called auto-aligning processes in the manufacturing of the substrates. In those processes, to obtain an enforced alignment of adjoining surfaces of adjacent substrates the same masks are used in each case for structuring the surfaces or for applying marks to those surfaces. For example, a registration structure can be produced by using a positive photoresist on the surface of the one substrate and a negative photoresist on the surface of the other substrate, exposing both photoresists on the relevant substrates using the same masks, developing the resists and subsequently etching a local depression (positive resist) on the one surface and an exactly corresponding elevation, by mesa etching, (negative resist) on the other surface. Instead of using complementary resist systems, other methods are also conceivable, for example deposition on a surface of the one substrate masked by the resist and an etching step on the surface of the other substrate marked by the resist. Among such auto-aligning or enforced alignment processes it is conceivable for stop edges, V grooves or guide pins to be provided on one substrate, with suitable complementary structures being formed on the other substrate. Owing to the possibility of using lithographic processes employing the same masks to create the alignment structures, an extremely precise and simple enforced alignment of the individual substrates with one another is achieved.

In addition to having the improved optical emission light source in the form of the surface-emitting laser, the structure shown in FIG. 5 also has the advantage of a modular construction using the plurality of planar substrates which can stacked on top of one another in register in a simple manner. Accordingly, to carry out measurements rapidly, the uppermost tier, which contains the sensor layers 309 and 319, can be removed each time after being consumed by a measurement and replaced by a new tier containing suitably selected sensor layers.

The structure shown in FIG. 5 has the advantage of a very compact transmission/receiver module, it being possible for the lateral position arrangement of all the lasers and photo-detectors to be determined very precisely by a common lithography process. Owing to the high integration density on the substrate 312, the relatively expensive gallium arsenide substrate material is handled in a very space-saving manner. Whereas only two surface-emitting semiconductor lasers and two corresponding photodetectors are shown in FIG. 5, it will be obvious that a considerably larger array can be produced at any time. Repeat distances in the region of 200 μm for successive surface-emitting semiconductor lasers can currently be achieved in practice.

Figure 6:
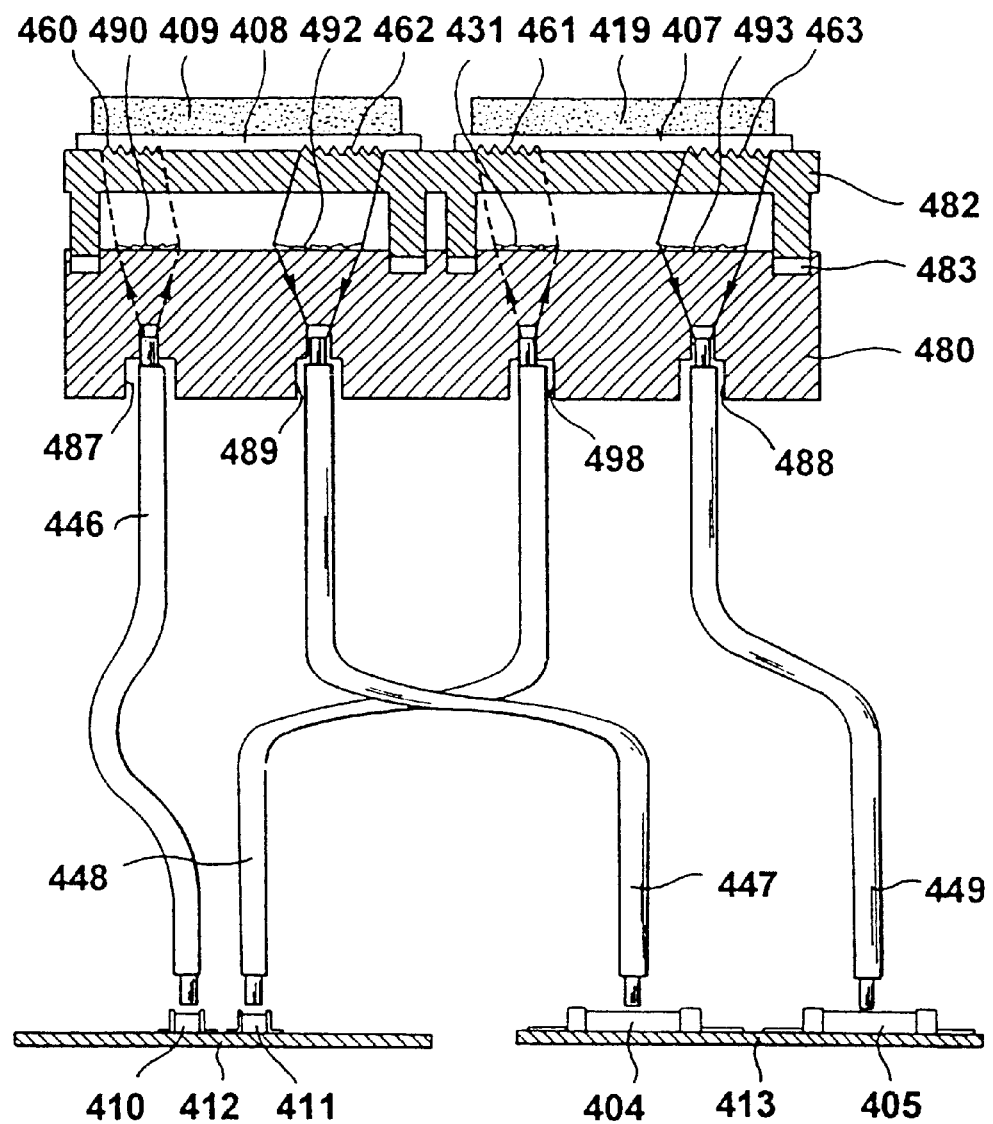
FIG. 6 is a cross-sectional view of a third embodiment of the detection device according to the invention.

In FIG. 6, a cross-section through a third embodiment of the optical detection device according to the invention is shown. Parts appearing in FIG. 6 that correspond to those already shown and described in FIG. 5 are identified by the same reference numerals increased, however, by 100. A description of parts already appearing in FIG. 5 and described with reference thereto will be dispensed with for the embodiment shown in FIG. 6.

The third embodiment shown in FIG. 6 differs from the second embodiment described here-inbefore by the fact that, on the one hand, the surface-emitting semiconductor lasers 410 and 411 and the photodetectors 404 and 405 are provided on separate substrates 412 and 413. For allocating the emission light to the coupling-in gratings 460 and 461 and the light coupled out of the waveguides, via the coupling-out gratings 462 and 463, to the corresponding photodetectors, instead of the substrate shown in FIG. 5 which has, the associated components that cause a widening of the beam on its first and second surface, in this case beam control using optical waveguides 446, 448 for the light emitted by the lasers and optical waveguides 447 and 449 for the light passed to the photodetectors is provided. At the locations respectively opposite the coupling-in gratings 460 and ,461 and the coupling-out gratings 462 and 463, the substrate 480 has beam-collimating elements 490, 491, 492 and 493. At the locations corresponding to the beam-collimating elements, and lying on the opposite side of the substrate 480, means 487, 498 and 488, 489 are provided for connection of the ends of the optical fibres 446, 447, 448, 449.

The use of glass fibers for supplying and removing the light between the wave guides adjoining the sensor layers and the surface-emitting lasers and the photo detectors means that the alignment of the individual optical elements on the relevant substrates is not problematica. Furthermore, array sizes in the region of from 1000 to 10,000 elements are possible. In addition, the array of photodetectors can be formed on silicon substrates, which are easier to handle and are available in larger substrate sizes. In this embodiment, the good beam quality of the surface-emitting semiconductor lasers shows its to advantage, leading to a high coupling-in efficiency into the optical fibers. By using glass fibers in this embodiment, the alignment of the semiconductor lasers and the photo diodes with the waveguides used for the measurement is simplified, since only a single registration step is required when mounting the waveguides on the photoelectric components. In addition, the coupling-in efficiency from the surface-emitting semiconductor lasers into the optical waveguides is very high since the coupling-in surfaces of the optical waveguides lie opposite the light outlet surfaces of the surface-emitting semiconductor lasers in virtually parallel relationship.

The use of fiber optics in accordance with the third embodiment further provides the advantage that little crosstalk occurs between the individual optical paths of the respective measuring zones. In addition, the design of the optical detection device can be more flexible, since a relatively wide physical separation of electrooptics and measuring cell is possible.

Figure 7:
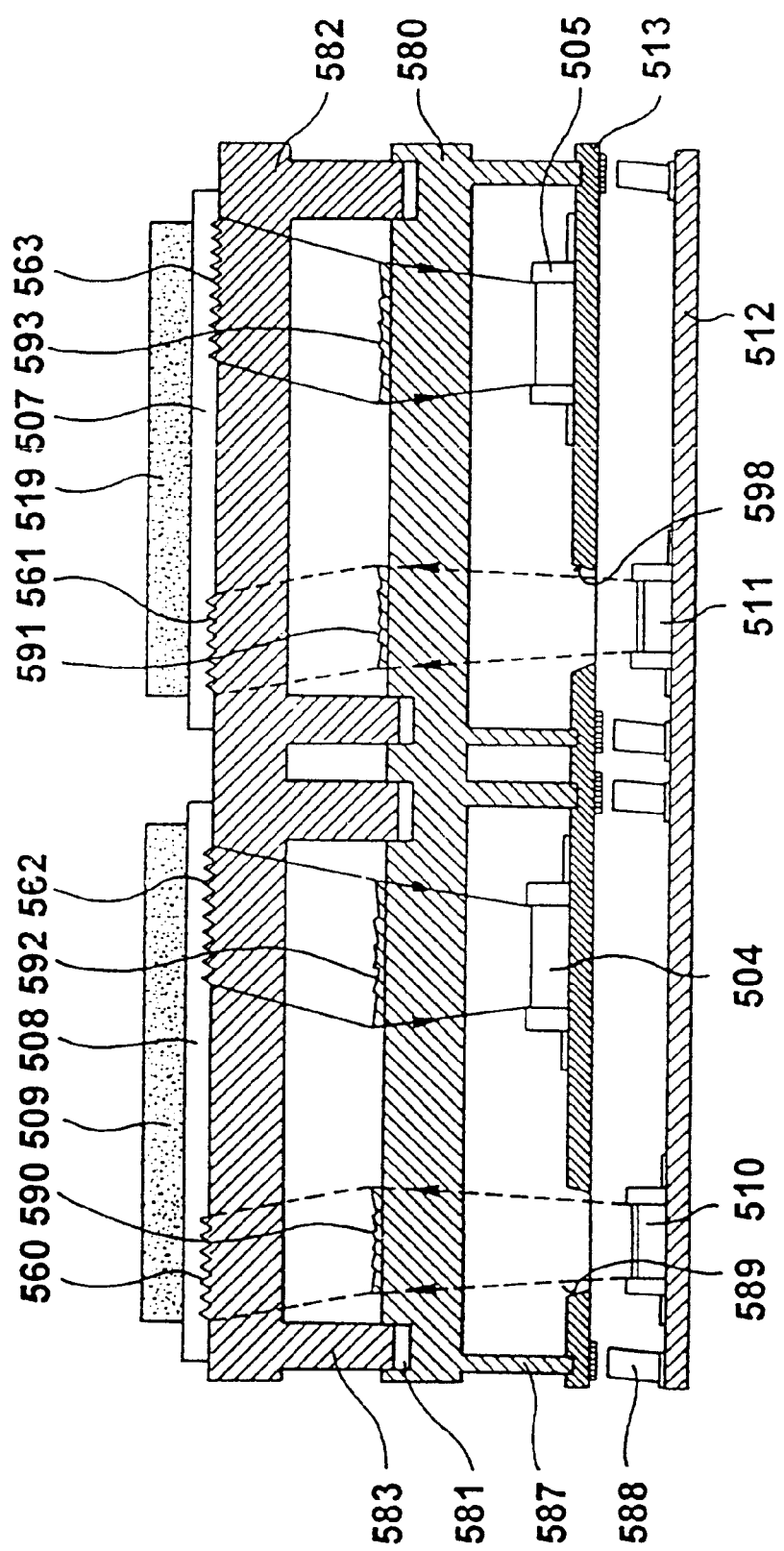
FIG. 7 is a cross-sectional view of a fourth embodiment of the detection device according to the invention.

A fourth embodiment of the optical detection device according to the invention will be described below with reference to FIG. 7. Elements of the fourth embodiment in FIG. 7 that correspond to elements in the second embodiment described with reference to FIG. 5 will again be identified by the same reference numerals increased, however, by 200. A detailed description of those elements will be dispensed with with reference to FIG. 7.

In the fourth embodiment, the surface-emitting semiconductor lasers 510 and 511 and the photodetectors 504 and 505 are respectively provided on their own substrates 512 and 513. The substrates 512 and 513 are not arranged side-by-side, however, but are arranged one above the other, thereby making it necessary for the substrate 513 that is arranged above the substrate 512 carrying the surface-emitting lasers to have through-openings, so-called via-holes, 589 and 598 which allow the light rays emitted by the surface-emitting lasers 510 and 511 to pass to the collimating optical elements 590 and 591. For attaching the lowermost substrate 512 to the substrate 513 above it in an aligned and non-destructive manner, spacing and registration means 588 are provided on the substrate 512, which again may be produced by auto-aligning processes. In addition, the substrate 580 carrying the collimating optical elements has projections 587 which serve to connect the substrates 580 and 513 in register.

The fourth embodiment has the advantage of relatively simple registration of the electro-optical and passive optical elements with one another. Furthermore, only a relatively simple optical system in the form of collimating elements arranged opposite the electrooptical elements is necessary. The overall structure has a very compact and space-saving construction.

Figure 8:
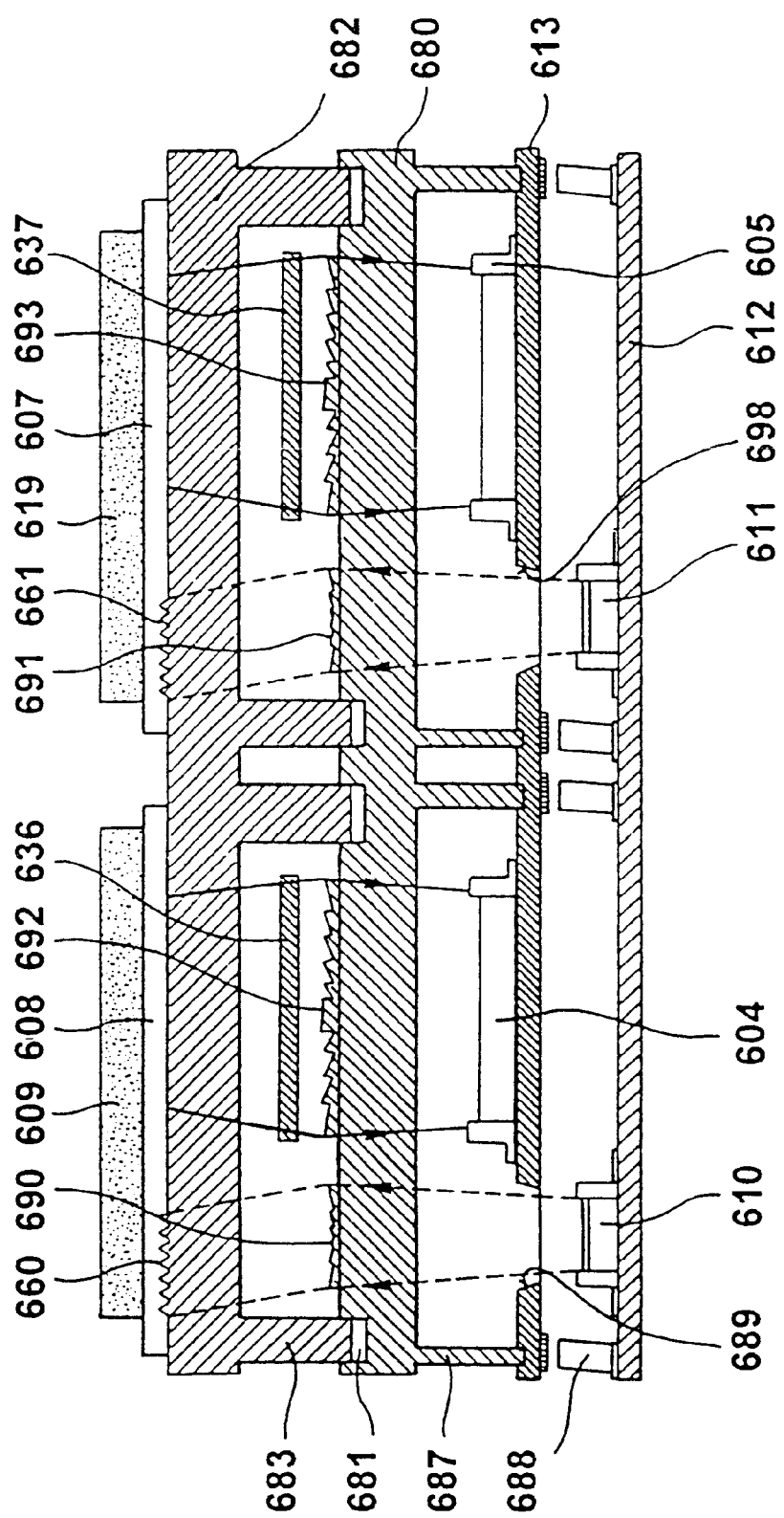
FIG. 8 is a cross-sectional view of a fifth embodiment of the detection device according to the invention.

In FIG. 8, a fifth embodiment of the optical detection device according to the invention is shown, elements appearing in FIG. 8 that have already been shown and described with reference to FIG. 7 being identified by the same reference numerals increased, however, by 100. A detailed description of such elements will be dispensed with with reference to FIG. 8. The fifth embodiment shown in FIG. 8 differs from the fourth embodiment according to FIG. 7 essentially by the fact that a "volume detection" is being carried out, that is to say the fluorescence light excited in the evanescent field of the waveguide but radiated isotropically is measured. It is not absolutely necessary, therefore, to provide a coupling-out grating in the fifth embodiment. On the other hand, such a coupling-out grating is not excluded, however, since it could serve, in particular, to couple out the transmitted excitation light as a reference signal or to determine the absorption.

In this fifth embodiment, filters, preferably interference filters, 636 and 637 are provided in each case between the waveguides 608 and 607 and the associated photodetectors 604 and 605. The position of the filters 636 and 637 between the substrates 680 and 682 is merely illustrative, it being clear to the person skilled in the art that the filters can be provided at any other location in the beam path between the waveguides and the corresponding photodiodes. The interference filters filter out the excitation light that is scattered in the upper substrate, the waveguide and the sensor layer towards the photodiode and allow only the desired luminescence emission to pass through.

Although the use of interference filters has been illustrated only in relation to the fifth embodiment, it will be obvious to the person skilled in the art that interference filters can also be provided, if necessary, in the first to fourth embodiments of the present invention. The third, fourth and fifth embodiments of the invention, shown in FIGS. 6, 7 and 8, respectively, use separate substrates for the array of semiconductor lasers and the array of photodiodes, as a result of which it is advantageously possible to provide the photodiodes on relatively cheap, customarily available silicon substrates. Owing to the reduced demand for relatively expensive gallium arsenide substrate surface, therefore, the costs of the detection device according to the invention can be further reduced.

In all the embodiments using a surface-emitting semiconductor laser that have been shown so far, it is possible in principle to measure and monitor the light power radiated by the surface-emitting semiconductor laser using a photodiode integrated under the rear-side Bragg mirror and use it for reference purposes. A monitor diode of that kind can easily be integrated in the gallium arsenide substrate during production of the individual surface-emitting semiconductor lasers or the array thereof.

Figure 9:
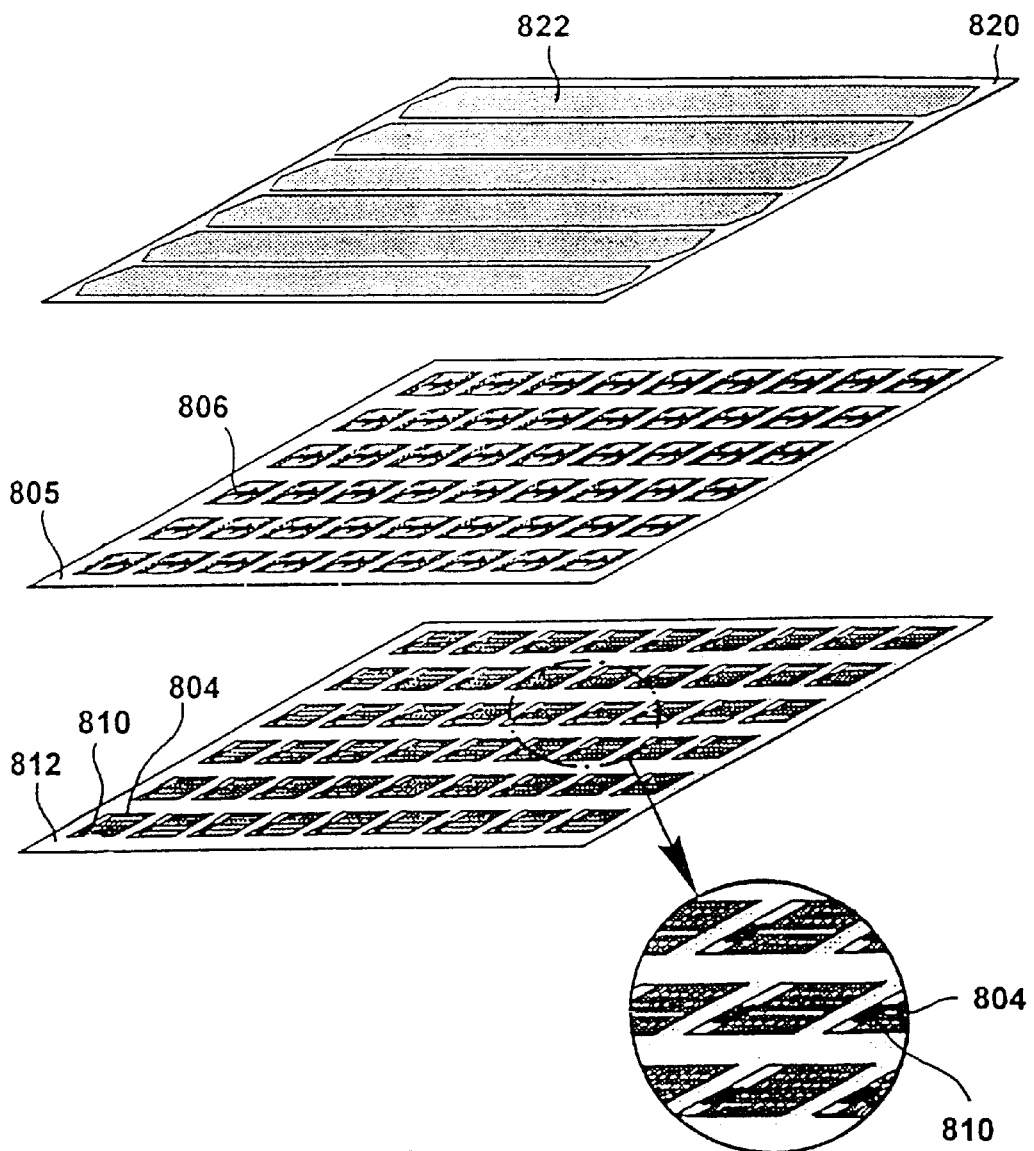
FIG. 9 is a schematic representation of a multi-channel sensor system according to the invention.

FIG. 9 shows, in a schematic exploded view, the basic construction of detector system suitable for chemical affinity assays. An uppermost layer 820, which is in contact with the measuring cell, contains replicated, parallel polymer strips 822. The polymer structures may also be provided in the manner of a chessboard. The layer containing the polymer structures is provided in the form of an easily fitted and removed single-use module.

Provided under the module containing the polymer structures is a layer having the sensor structures, hereinafter referred to as the sensor platform, which is likewise preferably in the form of a removable single-use module. The sensor platform comprises a two-dimensional array of waveguide films 806, preferably waveguide films having a high refractive index, which are constructed on replicated polymer films. Also present in that layer are coupling-in gratings, preferably provided in the polymer or, if the polymer is not used, in the substrate, and, on the other side of the substrate, microlenses preferably associated with each sensor element may be constructed.

Constructed in the third and lowermost layer is the excitation and detection module 812. This lowermost module comprises a corresponding array of individually addressable semi-conductor lasers 810 and corresponding photodiodes 804.

Using the arrangement of a multi-channel fluorescence sensor system illustrated in principle in FIG. 9, it is possible to analyse so-called "libraries" of the kind used in combinatorial chemistry. In such libraries, large quantities of different substances (ligands for target molecules) are synthesised. Those substances are synthesised on a random basis by iterative and automated solid-phase synthesis on the surface of polymer beads having typical diameters of from 50 to 100 $\mu$m. The multi-channel fluorescence detector device shown in principle in FIG. 9 is for the first time capable of fully exploiting the potential of such libraries in combinatorial chemistry to reduce the development times in the process for discovering new pharmaceuticals, owing to the increased processing speed and the multi-channel capabilities in the region of from 1000 to 10,000 parallel channels. A system of that kind therefore makes possible an extremely high sample throughput with minimum space requirements, so that such libraries or assays of combinatorial chemistry become possible and practicable.

For use as a chemical sensor, preferably one or more specific binding partners are selectively immobilized on the sensor platform as chemical or biochemical recognition elements for one or more, identical or different analytes forming at least one interaction region. Various specific binding partners can be applied to the surface of a waveguide, the physical separation thereof on a corresponding waveguide being unimportant. The various binding partners may, for example, be present on the waveguide in the form of a random mixture. That is advantageous, especially when analytes having different emission wavelengths are to be determined simultaneously by way of one coupling-out grating.

The specific binding partners can be immobilized at various sites on the waveguides, for example by photochemical crosslinking, as described, for example, in WO 94/27137. Another method comprises the dropwise application of the specific binding partners that are to be immobilized, using a multiple-pipette head. That can also be effected using a modified inkjet printing head with piezoelectric actuators. That has the advantage that the method can be carried out rapidly and that very small amounts can be used. That is a prerequisite for the production of thin strips or other finely structured geometric patterns.

It is, however, especially preferred in the case of the sensor platform to arrange only one specific binding partner on the surface of a single waveguide. A preferred method for the physically separate immobilization of the specific binding partners on the waveguides that is very simple to carry out is based on the use of a flow cell, it being possible for the separation to be effected in the flow cell either mechanically in the form of partitioning bars or fluidically in the case of laminar flow. In that method, the geometric arrangement of the part streams supplying the binding partners corresponds substantially to the arrangement of the waveguiding regions on the sensor platform. That method of immobilization using a flow cell is advantageous especially when the specific binding partners are to be embedded in an environment that is stable only in the fluid medium, as is the case, for example, with lipid-membrane-bound receptors. In particular, it is possible in that manner to deposit specific binding partners that are covalently bonded to gold colloids, for example by deposition from aqueous chemical solutions. In that process, physically or fluidically separate laminar part streams of a colloidal gold solution are allowed to flow over the waveguide, the gold particles being deposited, for example, in the form of strips.

Another method of providing the specific binding partners on the waveguides that is likewise simple to carry out is based on stamping the surface of the waveguides with specific binding partners bonded to gold. The stamping is carried out by so-called "microcontact printing" by means of elastomeric stamps having the desired structuring profile which soak up the colloidal gold solution and transfer it to the waveguide on application of the stamp. Preferred physically separate patterns are strips, rectangles, circles, ellipses or chessboard patterns.

It is also especially advantageous to provide an adhesion-promoting layer between the waveguides and the immobilized specific binding partners. To obtain better adhesion, it is advantageous to treat the surface of the waveguide, before deposition of the gold colloids, in a suitable manner to obtain increased adhesiveness. The improvement in adhesion can be achieved by means of hydrophobic interaction, van der Waals forces, dipole-dipole inter-action, simple electrostatic interaction or covalent bonding. The interaction can also be produced by functionalisation of the colloids and/or the surface of the waveguiding layer. A suitable method of modifying the surface of the waveguide and of improving adhesion of the gold colloids comprises, for example, silanisation of the waveguide surface.

The thickness of the adhesion-promoting layer is preferably not more than 50 nm and is especially less than 20 nm. The adhesion-promoting layers may be applied selectively to the waveguides alone using wet chemical processes, for example using multiple-pipette heads, an inkjet printer, flow cells with mechanical and fluidic separation of the streams, deposition of colloids or stamping onto the surface. If the adhesion-promoting layers are applied over the entire surface area, passivation may also take place, for example by means of photochemical treatment, in the regions surrounding the waveguides.

The selective immobilization of the specific recognition elements exclusively on the wave-guiding regions, either directly or by way of adhesion-promoting layers, can, when using a sample cell that covers both the waveguiding and the non-waveguiding regions, lead to an increase in the sensitivity of the detection method, since the non-specific binding of the analyte in the regions not used for signal generation is reduced.

The sensor platform is preferably fully or partially regenerable and can be used several times. Under suitable conditions, for example at low pH, at elevated temperature, using organic solvents or using so-called chaotropic reagents (salts), the affinity complexes can be selectively dissociated without impairing the binding ability of the immobilized recognition elements to any appreciable extent. The precise conditions are greatly dependent upon the particular affinity system.

A specific form of luminescence detection in an assay consists in the immobilization of the luminescent substances that are used for detection of the analyte directly on the surface of the waveguides. Those substances may be, for example, a plurality of luminophores bound to a protein, which can in that manner be excited to luminescence on the surface of the waveguides. If partners having affinity for the proteins are passed over that immobilized layer, the luminescence can be altered thereby and the quantity of the partners having affinity can thus be determined. In particular, it is also possible for both partners of an affinity complex to be labelled with luminophores in order, for example, to carry out determinations of concentration on the basis of the energy transfer between the two, for example in the form of luminescence extinction.

Another preferred form of immobilization for chemical or biochemical affinity assays consists in the immobilization on the surface of the sensor platform of one or more specific binding partners as chemical or biochemical recognition elements for the analytes themselves or for a binding partner. The assays may consist of one or more stages in the course of which, in successive steps, one or more solutions containing specific binding partners of the recognition elements immobilized on the surface of the sensor platform are passed over the surface of the sensor platform, the analytes being bound in one of the part steps. The analytes are detected by the binding of luminescently labelled participants in the affinity assays. The luminescence-labelled substances used therein may be any one or more of the binding partners of the affinity assay, or an analogue of the analytes provided with a luminophore. The only prerequisite is that the presence of the analytes should lead selectively to a luminescence signal or selectively to a change in the luminescence signals.

The recognition elements can be immobilized, for example, by hydrophobic adsorption or covalent bonding directly on the waveguiding region or after chemical modification of the surface, for example by silanisation or the application of a polymer layer. In addition, in order to facilitate the immobilization of the recognition elements directly on the waveguide, a thin intermediate layer, for example consisting of $SiO_2$, can be applied as an adhesion-promoting layer. The silanisation of glass and metal surfaces has been described comprehensively in the literature, for example in "Advances in Colloid and Interface Science 6", L. Boksányi, O. Liardon and E. Kováts, (1976) 95–137.

Suitable recognition elements are, for example, antibodies for antigens, binding proteins, such as protein A and G, for immunoglobulins, biological and chemical receptors for ligands, oligonucleotides and single strands of RNA and DNA for their complementary strands, avidin for biotin, enzymes for enzyme substrates, enzyme cofactors or inhibitors, or lectins for carbohydrates. Which of the relevant affinity partners is immobilized on the surface of the sensor platform depends upon the architecture of the assay.

The assays themselves may be either one-step complexing processes, for example competitive assays, or multi-step processes, for example sandwich assays.

In the simplest example of a competitive assay, the sample, which comprises the analyte in unknown concentration and a known amount of a compound that is identical apart from being luminescence-labelled, is brought into contact with the surface of the sensor platform, where the luminescence-labelled and unlabelled molecules compete for the binding sites on their immobilized recognition elements. In this assay configuration, a maximum luminescence signal is obtained when the sample contains no analyte. As the concentration of the substance to be detected increases, the observable luminescence signals decrease.

In a competitive immunoassay, the recognition element immobilized on the surface of the sensor platform does not have to be the antibody but may alternatively be the antigen. It is generally a matter of choice in chemical or biochemical affinity assays which of the partners is immobilized. That is a fundamental advantage of assays based on luminescence over methods such as surface plasmon resonance or interferometry which rely on a change in the adsorbed mass in the evanescent field of the waveguide.

Furthermore, the competition in the case of competitive assays need not be limited to binding sites on the surface of the sensor platform. For example, a known amount of an antigen can be immobilized on the surface of the sensor platform and then brought into contact with the sample which comprises as analyte an unknown amount, which is to be detected, of the same antigen and also luminescence-labelled antibodies. In that case, the competition to bind the antibodies takes place between antigens immobilized on the surface and antigens in solution.

The simplest example of a multi-step assay is a sandwich immunoassay in which a primary antibody is immobilized on the surface of the sensor platform. The binding of the antigen to be detected and of the luminescence-labelled secondary antibody used for the detection to a second epitope of the antigen can be effected either by contact with, in succession, the solution comprising the antigen and a second solution comprising the luminescence-labelled antibody or after previously bringing the two solutions together so that finally the part-complex consisting of antigen and luminescence-labelled antibody is bound.

Affinity assays may also comprise further additional binding steps. For example, in the case of sandwich immunoassays, in a first step protein A can be immobilized on the surface of the sensor platform. The protein specifically binds immunoglobulins to its so-called $F_c$ portion and these then serve as primary antibodies in a subsequent sandwich assay. There are many other forms of affinity assay, for example using the known avidin-biotin affinity system. Examples of forms of affinity assay are to be found in J. H. Rittenburg, Fundamentals of Immunoassay; in Development and Application of Immunoassay for Food Analysis, J. H. Rittenburg (Editor), Elsevier, Essex 1990, or in P. Tijssen, Practice and Theory of Enzyme Immunoassays, R. H. Burdon, P. H. van Knippenberg (Editors), Elsevier, Amsterdam 1985.

By "sample" there is to be understood within the context of the present invention the entire solution to be analyzed, which may comprise a substance to be detected—the analyte. The detection can be effected in a one-step or multiple-step assay during the course of which the surface of the sensor layer is brought into contact with one or more solutions. At least one of the solutions used comprises a luminescent substance which can be detected.

If a luminescent substance is already present in the sensor layer, the sample may also be free of luminescent constituents. The sample may contain further constituents, such as pH buffers, salts, acids, bases, surfactants, viscosity-influencing additives or dyes. In particular, a physiological saline solution can be used as solvent. If the luminescent portion is itself liquid, the addition of a solvent can be omitted. In that case the content of luminescent substance in the sample may be up to 100%.

The sample may especially be a biological medium, such as egg yolk, a body fluid or constituents thereof, especially blood, serum, plasma or urine. It may also be surface water, solutions of extracts from natural or synthetic media, such as soils or parts of plants, liquors from biological processes or liquors from syntheses. The sample may be used either undiluted or with added solvent.

Suitable solvents are water, aqueous buffer solutions and protein solutions and organic solvents. Suitable organic solvents are alcohols, ketones, esters and aliphatic hydrocarbons. Preference is given to the use of water, aqueous buffers or a mixture of water with a miscible organic solvent.

The sample may, however, also comprise constituents that are not soluble in the solvent, such as pigment particles, dispersants and natural and synthetic oligomers or polymers. The sample is then in the form of an optically opaque dispersion or emulsion.

There may be used as luminescent compounds luminescent dyes having a luminescence of a wavelength in the range of from 330 nm to 1000 nm, such as rhodamines, fluorescein derivatives, coumarin derivatives, distyryl biphenyls, stilbene derivatives, phthalo cyanines, naphthalocyanines, polypyridyl/ruthenium complexes, such as tris(2,2'-bipyridyl) ruthenium chloride, tris(1,10-phenanthroline)ruthenium chloride, tris(4,7-diphenyl-1,10-phenanthroline)ruthenium chloride and polypyridyl/phenazine/ruthenium complexes, platinum/porphyrin complexes, such as octaethyl-platinum-porphyrin, long-lived europium and terbium complexes or cyanine dyes. Especially suitable for analyses in blood or serum are dyes having absorption and emission wavelengths in the range of from 600 to 900 nm.

Very especially suitable are dyes, such as fluorescein derivatives, containing functional groups by means of which they can be covalently bonded, such as fluorescein isothiocyanate. The preferred luminescence is fluorescence.

The luminescent dyes used may also be chemically bonded to polymers or to one of the binding partners in biochemical affinity systems, for example antibodies or antibody fragments, antigens, proteins, peptides, receptors or their ligands, hormones or hormone receptors, oligonucleotides, DNA strands and RNA strands, DNA or RNA analogues, binding proteins, such as protein A and G, avidin or biotin, enzymes, enzyme cofactors or inhibitors, lectins or carbohydrates. The use of the last-mentioned covalent luminescence labelling is preferred for reversible or irreversible (bio)chemical affinity assays. It is also possible to use luminescence-labelled steroids, lipids and chelators. In the case especially of hybridisation assays with DNA strands or oligonucleotides, intercalating luminescent dyes are also especially suitable, especially when—like various ruthenium complexes—they exhibit enhanced luminescence when intercalated. When those luminescence-labeled compounds are brought into contact with their affinity partners immobilized on the surface of the sensor platform, their binding can easily be quantitatively determined by reference to the measured luminescence intensity. Equally, quantitative determination of the analytes is possible by measuring the change in luminescence when the sample interacts with the luminophores, for example in the form of luminescence extinction by oxygen or luminescence enhancement resulting from conformation changes in proteins.

What is claimed is:

1. An optical detection device, comprising:

a substrate;

at least one light source comprising a single wavelength surface-emitting semiconductor laser and being operable to emit detection light, said at least one light source being located on said substrate;

at least one photoelectric detection unit operable to detect a light intensity and to convert the light intensity into a corresponding electrical signal, said at least one photoelectric detection unit being located on said substrate;

at least one measuring cell operable to hold a sample to be examined;

at least one optical path comprising a planar waveguide and being coupled to said at least one measuring cell and formed between said at least one light source and said at least one photoelectric detection unit, wherein said at least one planar waveguide allows the detection light to pass through and excite an evanescent field; and at least one specific binding partner operable to act as a recognition element for at least one analyte, said at least one specific binding partner being immobilized on said at least one planar waveguide and forming at least one interaction region.

2. An optical detection device according to claim 1, wherein said at least one light source comprises a plurality of single wavelength surface-emitting semiconductor lasers provided on a common substrate.

3. An optical detection device according to claim 1, wherein said at least one single wavelength surface-emitting semiconductor laser is operable to emit visible light for use in fluorescence spectroscopy.

4. An optical detection device according to claim 3, wherein said at least one single wavelength surface-emitting semiconductor laser comprises a plurality of regions and at least one region of said plurality of regions forms a Bragg mirror and said at least one region comprises a plurality of layers, wherein adjacent layers of said plurality of layers have stoichiometric compositions that change in a continuous manner.

5. An optical detection device according to claim 4 wherein the continuous change of the stoichiometric compositions of said adjacent layers is linear.

6. An optical detection device according to claim 1, wherein said at least one single wavelength surface-emitting semiconductor laser is formed on a substrate and is defined by mesa etching.

7. An optical detection device according to claim 6, wherein said at least one mesa etched single wavelength surface-emitting semiconductor laser comprises an upper surface containing an emission window and flanks, said emission window oriented perpendicularly to said substrate, and said flanks and said upper surface, except for said emission window, are covered by a metal layer.

8. An optical detection device according to claim 7, wherein said at least one mesa etched single wavelength surface-emitting semiconductor laser further comprises an electrical contacting layer, wherein said metal layer is identical with said electrical contacting layer.

9. An optical detection device according to claim 1, further comprising at least one monitoring detection device, each of said at least one monitoring detection device corresponding to one of said at least one light source and being operable to monitor an actual detection light intensity of the detection light emitted by said corresponding one of said at least one light source.

10. An optical detection device according to claim 1, wherein said at least one light source, said at least one photoelectric detection unit, and said at least one optical path are formed on first, second, and third substrates, respectively, wherein said first, second, and third substrates are substantially planar.

11. An optical detection device according to claim 10, wherein said first, second, and third substrates are stacked on top of each other.

12. An optical detection device according to claim 11, wherein said first, second, and third substrates each have registration structures for mutual alignment.

13. An optical detection device according to claim 12, wherein said registration structures are produced using auto-aligning processes.

14. An optical detection:device according to claim 10, further comprising:
coupling-in elements located on said third substrate operable to bend the detection light emitted by said at least one light source into a direction that is substantially parallel to a surface of said third substrate towards said at least one measuring cell, for interaction of immobilized specific binding partners for an analyte, forming at least one interaction region in said at least one measuring cell; and
coupling-out elements located on said third substrate operable to bend the light towards said at least one photoelectric detection unit formed on said second substrate after passing said at least one measuring cell, and after interaction of said immobilized specific binding partners with a sample to be examined.

15. An optical detection device according to claim 14, further comprising:
a fourth substrate arranged between said second and third substrates;
first optical elements provided on said fourth substrate operable to collimate and bend the detection light emitted from said at least one light source; and
second optical elements provided on said fourth substrate operable to collimate and bend light emerging after interacting with the at least one sample, in said at least one interaction region, onto said at least one photoelectric detection unit.

16. An optical detection device according to claim 1, wherein said at least one light source is an array of single wavelength surface-emitting semiconductor lasers and said at least one photoelectric detection unit is an array of photoelectric detection units, said array of single wavelength surface-emitting semiconductor lasers having a density greater than a density of said at least one interaction region.

17. An optical detection device according to claim 16, further comprising means for matching a density of the light beams emitted by said array of single wavelength surface-emitting semiconductor lasers to the density of said at least one interaction region.

18. An optical detection device according to claim 17, wherein said means for matching comprise an array of optical fibers, each of said optical fibers having input and output ends and cooperating with a respective one of said array of single wavelength surface-emitting semiconductor lasers, said output ends being spread out in comparison with said input ends in accordance with the density of said at least one interaction region.

19. An optical detection device according to claim 17, further comprising an array of coupling-in elements, each of said coupling-in elements being associated with a respective one of said array of single wavelength surface-emitting semiconductor lasers, wherein said means for matching comprise an array of first optical elements, each of said first optical elements being associated with a respective one of said array of single wavelength surface-emitting semiconductor lasers and being operable to bend the light beam emitted by said respective one of said array of single wavelength surface-emitting semiconductor lasers in a direction substantially perpendicular to a surface of said respective one of said array of single wavelength surface-emitting semiconductor lasers into a direction such that the light beam impinges on a corresponding coupling-in element of said array of coupling-in elements to be coupled into said at least one optical path.

20. An optical detection device according to claim 19, further comprising second optical elements operable to return the light beams of said array of single wavelength surface-emitting semiconductor lasers that have been bent by said array of first optical elements into a direction substantially perpendicular to the surface of said respective one of said array of single wavelength surface-emitting semiconductor lasers.

21. An optical detection device according to claim 1 wherein said at least one light source and said at least one photoelectric detection unit are provided on a common substrate.

22. An optical detection device according to claim 21, wherein said at least one light source and said at least one photoelectric detection unit are arranged on said common substrate in the form of intermeshing, mutually corresponding arrays.

23. An optical detection device according to claim 1, wherein said at least one planar waveguide is structured to guide from one to three modes.

24. An optical detection device according to claim 1, wherein said at least one planar waveguide is made from a material having a high refractive index.

25. An optical detection device according to claim 24 wherein said material comprises at least one of titanium dioxide and tantalum pentoxide.

26. An optical detection device according to claim 1, wherein said at least one specific binding partner forms a sensor layer provided on said at least one planar waveguide and is operable to be selectively sensitive to at least one analyte to be examined in the at least one sample.

27. An optical detection device according to claim 26, wherein said at least one specific binding partner comprises a plurality of binding partners physically separated from each other.

28. An optical detection device according to claim 26, wherein said at least one specific binding partner comprises a plurality of specific binding partners, and wherein not more than one of said plurality of specific binding partners is arranged on a surface of said at least one planar waveguide.

29. An optical detection device according to claim 1, further comprising an adhesion-promoting layer, wherein said adhesion-promotion layer is located between said at least one planar waveguide and said at least one specific binding partner.

30. An optical detection device according to claim 1, wherein said at least one specific binding partner comprises a plurality of specific binding partners covalently bonded to gold colloids, wherein said gold colloids are smaller than 10 nm.

31. An optical detection device according to claim 1, wherein said substrate is coupled directly to said at least one optical path.

32. An optical detection device according to claim 1, further comprising a housing, wherein said housing is located between said substrate and said at least one optical path.

33. An optical detection device, comprising:
   a substrate;
   a plurality of light sources comprising at least one linear arrangement of single wavelength edge-emitting semiconductor lasers produced on a common substrate and each being operable to emit a detection light, said plurality of light sources being located on said substrate;
   a corresponding plurality of photoelectric detection units, each associated with a corresponding light source of said plurality of light sources, and each operable to detect a light intensity and to convert the light intensity into a corresponding electrical signal, said corresponding plurality of photoelectric detection units being located on said substrate;
   at least one measuring cell operable to hold a sample to be examined;
   a plurality of optical paths, each comprising a planar waveguide and being coupled to said at least one measuring cell, and each being formed between said plurality of light sources and said corresponding plurality of photoelectric detection units, wherein said plurality of planar waveguides allow the detection lights to pass through and excite an evanescent field; and
   at least one specific binding partner operable to act as a recognition element for at least one analyte, said at least one specific binding partner being immobilized on at least one of said plurality of planar waveguides and forming at least one interaction region.

34. An optical detection device according to claim 33, wherein each of said plurality of light sources is associated with one of said corresponding plurality of photoelectric detection units and one of said plurality of optical paths.

35. An optical detection device according to claim 33, wherein each of said plurality of light sources is associated with exactly one of said plurality of said photoelectric detection units and exactly one of said plurality of optical paths.

36. An optical detection device according to claim 33, further comprising a plurality of monitoring detection devices, each of said plurality of monitoring detection devices corresponding to one of said plurality of light sources and being operable to monitor an actual detection light intensity of the detection light emitted by said one of said corresponding plurality of light sources.

37. An optical detection device according to claim 33, wherein said plurality of light sources, said plurality of photoelectric detection units, and said plurality of optical paths are formed on first, second, and third substrates, respectively, wherein said first, second, and third substrates are substantially planar.

38. An optical detection device according to claim 37, wherein said first, second, and third substrates are stacked on top of each other.

39. An optical detection device according to claim 38 wherein said first, second, and third substrates each have registration structures for mutual alignment.

40. An optical detection device according to claim 39, wherein said registration structures are produced using auto-aligning processes.

41. An optical detection device according to claim 37, further comprising:
   coupling-in elements located on said third substrate operable to bend the detection light emitted by said plurality of light sources into a direction that is substantially parallel to a surface of said third substrate towards said at least one measuring cell, for interaction of immobilized specific binding partners for an analyte, forming at least one interaction region in said at least one measuring cell; and
   coupling-out elements located on said third substrate operable to bend the light towards said plurality of photoelectric detection units formed on said second substrate after passing said at least one measuring cell and after interaction of said immobilized specific binding partners with a sample to be examined.

42. An optical detection device according to claim 41 further comprising:
   a fourth substrate arranged between said second and third substrates;
   first optical elements provided on said fourth substrate operable to collimate and bend the detection lights emitted from said plurality of light sources; and
   second optical elements provided on said fourth substrate operable to collimate and bend light emerging after interacting with the at least one sample, in said at least one interaction region, onto said plurality of photoelectric detection units.

43. An optical detection device according to claim 33, wherein said at least one linear arrangement of single wavelength edge-emitting semiconductor lasers is an array of single wavelength edge-emitting semiconductor lasers and said plurality of photoelectric detection units is an array of photoelectric detection units, said array of single wavelength edge-emitting semiconductor lasers having a density greater than a density of said at least one interaction region.

44. An optical detection device according to claim 43, further comprising means for matching the density of the light beams emitted by said array of single wavelength edge-emitting semiconductor lasers to the density of said at least one interaction region.

45. An optical detection device according to claim 44, wherein said means for matching comprise an array of optical fibers, each of said optical fibers having input and output ends and cooperating with a respective one of said array of single wavelength edge-emitting semiconductor lasers, said output ends being spread out in comparison with said input ends in accordance with the density of said at least one interaction region.

46. An optical detection device according to claim 44, further comprising an array of coupling-in elements, each of said coupling-in elements being associated with a respective one of said array of single wavelength edge-emitting semiconductor lasers, wherein said means for matching comprise an array of first optical elements, each of said first optical elements being associated with a respective one of said array of single wavelength edge-emitting semiconductor lasers and being operable to bend the light beam emitted by said respective one of said array of single wavelength edge-emitting semiconductor lasers in a direction substantially perpendicular to a surface of said respective one of said array of single wavelength edge-emitting semiconductor lasers into a direction such that the light beam impinges on a corresponding coupling-in element of said array of coupling-in elements to be coupled into said plurality of optical paths.

47. An optical detection device according to claim 46, further comprising second optical elements operable to return the light beams of said array of single wavelength edge-emitting semiconductor lasers that have been bent by said array of first optical elements into a direction substantially perpendicular to the surface of said respective one of said array of single wavelength edge-emitting semiconductor lasers.

48. An optical detection device according to claim 33, wherein said plurality of light sources and said plurality of photoelectric detection units are provided on a common substrate.

49. An optical detection device according to claim 48, wherein said plurality of light sources and said plurality of photoelectric detection units are arranged on said common substrate in the form of intermeshing, mutually corresponding arrays.

50. An optical detection device according to claim 33, wherein each of said plurality of planar waveguides is structured to guide from one to three modes.

51. An optical detection device according to claim 33, wherein said plurality of planar waveguides are made from a material having a high refractive index.

52. An optical detection device according to claim 51, wherein said material comprises at least one of titanium dioxide and tantalum pentoxide.

53. An optical detection device according to claim 33, wherein said at least one specific binding partner forms a sensor layer provided on said plurality of planar waveguides and is operable to be selectively sensitive to at least one analyte to be examined in the at least one sample.

54. An optical detection device according to claim 53, wherein said at least one specific binding partner comprises a plurality of binding partners physically separated from each other.

55. An optical detection device according to claim 53, wherein said at least one specific binding partner comprises a plurality of specific binding partners, and wherein not more than of the said plurality of specific binding partners is arranged on a surface of each of said plurality of planar waveguides.

56. An optical detection device according to claim 33, further comprising an adhesion-promoting layer, wherein said adhesion-promotion layer is located between said plurality of planar waveguides and said at least one specific binding partner.

57. An optical detection device according to claim 33, wherein said at least one specific binding partner comprises a plurality of specific binding partners covalently bonded to gold colloids, wherein said gold colloids are smaller than 10 nm.

58. An optical detection device according to claim 33, wherein said substrate is coupled directly to said plurality of optical paths.

59. An optical detection device according to claim 33, further comprising a housing, wherein said housing is located between said substrate and said plurality of optical paths.

60. A method for the parallel determination of one or more luminescences comprising:
providing at least one light source for emitting detection light, the at least one light source being located on a substrate;
providing at least one photoelectric detection unit for detecting a light intensity and converting the light intensity into a corresponding electrical signal, the at least one photoelectric detection unit being located on the substrate;
providing at least one measuring cell for holding a sample to be examined;
using at least one optical path to couple the at least one measuring cell being formed between the at least one light source and the at least one photoelectric detection unit to the at least one light source and the at least one photoelectric detection unit, wherein the at least one light source is a single wavelength surface-emitting semiconductor laser and wherein the at least one optical path comprises a planar waveguide which is coupled to the at least one measuring cell;
providing a sensor layer comprising at least one specific binding partner operable to act as a recognition element for at least one analyte on the at least one planar waveguide, the sensor layer being coupled to the at least one measuring cell and which is selectively sensitive to at least one analyte to be examined in the at least one sample;
bringing the at least one sample into contact with the at least one planar waveguide;
coupling excitation light into the at least one planar waveguide, causing the light to pass through the at least one planar waveguide, and thus, exciting in parallel in an evanescent field, at least one luminescent substance in the at least one sample, wherein the at least one luminescent substance is bound to an immobilized specific binding partner acting as a recognition element for the at least one analyte or to another specific binding partner bound to the immobilized specific binding partner on the at least one planar waveguide; and
measuring the one or more luminescences produced thereby using photoelectric detection elements.

61. A method for the parallel determination of one or more luminescence as claimed in claim 60, wherein the at least one luminescent substance comprises luminescent dyes from the group consisting of rhodamines, fluorescein derivatives, coumarin derivatives, distyryl biphenyls, stilbene derivatives, phthalo cyanines, naphthalocyanines, polypyridyl/ruthenium complexes, such as tris (2, 2'-bipyridyl) ruthenium chloride, tris (1, 10-phenanthroline) ruthenium chloride tris (4, 7-diphenyl-1, 10-phenanthroline) ruthenium chloride and polypyridyl/phenazine/ruthenium complexes, platinum/porphyrin complexes, europium and terbium complexes and cyanine dyes.

62. A method for the parallel determination of one or more luminescence as claimed in claim 60, wherein the at least one sample comprises at least one of egg yolk, blood, serum, plasma, and urine.

63. A method for the parallel determination of one or more luminescence as claimed in claim 60, wherein the at least one sample comprises at least one of surface water, a soil extract, a plant extract, a liquor from biological processes and a liquor from synthesis processes.

64. A method according to claim 60, wherein the substrate is coupled directly to the at least one optical path.

65. A method according to claim 60, wherein a housing is located between the substrate and the at least one optical path.

66. A method for the parallel determination of one or more luminescence, comprising:
  providing a plurality of light sources for emitting detection light, the plurality of light sources being located on a substrate;
  providing a corresponding plurality of photoelectric detection units, each associated with a corresponding light source, for detecting a light intensity and converting the light intensity into a corresponding electrical signal, the corresponding plurality of photoelectric detection units being located on the substrate;
  providing at least one measuring cell for holding a sample to be examined;
  using a plurality of optical paths each to couple the at least one measuring cell being formed between the light sources and the corresponding photoelectric detection units to the light sources and the corresponding photoelectric detection units and wherein the plurality of light sources comprises at least one linear arrangement of single wavelength edge-emitting semiconductor lasers produced on a common substrate and wherein each of the plurality of optical paths comprises a planar waveguide which is coupled to the at least one measuring cell;
  providing a sensor layer comprising at least one specific binding partner operable to act as a recognition element for at least one analyte on at least one of the plurality of planar waveguides, the sensor layer being coupled to the at least one measuring cell and being selectively sensitive to at least one analyte to be examined in the at least one sample;
  bringing the at least one sample into contact with the plurality of planar waveguides;
  coupling excitation light into the plurality of planar waveguides, causing the light to pass through the plurality of planar waveguides, and thus, exciting in parallel in an evanescent field, at least one luminescent substance in the at least one sample wherein, wherein the at least one luminescent substance is bound to an immobilized specific binding partner acting as a recognition element for the at least one analyte or to another specific binding partner bound to the immobilized specific binding partner on at least one of the plurality of planar waveguides; and
  measuring the one or more luminescences produced thereby using photoelectric detection elements.

67. A method for the parallel determination of one or more luminescence as claimed in claim 66, wherein the at least one luminescent substance comprises luminescent dyes from the group consisting of rhodamines, fluorescein derivatives, coumarin derivatives, distyryl biphenyls, stilbene derivatives, phthalo cyanines, naphthalocyanines, polypyridyl/ruthenium complexes, such as tris (2, 2'-bipyridyl) ruthenium chloride, tris (1, 10-phenanthroline) ruthenium chloride tris (4, 7-diphenyl-1, 10-phenanthroline) ruthenium chloride and polypyridyl/phenazine/ruthenium complexes, platinum/porphyrin complexes, europium and terbium complexes and cyanine dyes.

68. A method for the parallel determination of one or more luminescence as claimed in claim 66, wherein the at least one sample comprises at least one of egg yolk, blood, serum, plasma, and urine.

69. A method for the parallel determination of one or more luminescence as claimed in claim 66, wherein the at least one sample comprises at least one of surface water, a soil extract, a plant extract, a liquor from biological processes and a liquor from synthesis processes.

70. A method according to claim 66, wherein the substrate is coupled directly to the plurality of optical paths.

71. A method according to claim 66, wherein a housing is located between the substrate and the plurality of optical paths.

72. An optical detection device, comprising:
  at least one light source comprising a single wavelength surface-emitting semiconductor laser and being operable to emit detection light, said at least one light source being located on a first substrate;
  at least one photoelectric detection unit operable to detect a light intensity and to convert the light intensity into a corresponding electrical signal, said at least one photoelectric detection unit being located on a second substrate;
  at least one measuring cell operable to hold a sample to be examined;
  at least one optical path comprising a planar waveguide and being coupled to said at least one measuring cell and formed between said at least one light source and said at least one photoelectric detection unit, wherein said at least one planar waveguide allows the detection light to pass through and excite an evanescent field; and
  at least one specific binding partner operable to act as a recognition element for at least one analyte, said at least one specific binding partner being immobilized on said at least one planar waveguide and forming at least one interaction region,
  wherein said first substrate and said second substrate are located on a same side of said at least one optical path.

73. An optical detection device according to claim 72, wherein said first substrate and said second substrate are coupled directly to said at least one optical path.

74. An optical detection device according to claim 72, further comprising a housing, wherein said housing is located between said first and second substrates and said at least one optical path.

75. An optical detection device, comprising:
  a plurality of light sources comprising at least one linear arrangement of single wavelength edge-emitting semiconductor lasers produced on a common substrate and each being operable to emit a detection light, said plurality of light sources being located on a first substrate;
  a corresponding plurality of photoelectric detection units, each associated with a corresponding light source of said plurality of light sources, and each operable to detect a light intensity and to convert the light intensity into a corresponding electrical signal, said corresponding plurality of photoelectric detection units being located on a second substrate;
  at least one measuring cell operable to hold a sample to be examined;
  a plurality of optical paths, each comprising a planar waveguide and being coupled to said at least one measuring cell, and each being formed between said plurality of light sources and said corresponding plurality of photoelectric detection units, wherein said plurality of planar waveguides allow the detection lights to pass through and excite an evanescent field; and at least one specific binding partner operable to act as a recognition element for at least one analyte, said at least one specific binding partner being immobilized on at least one of said plurality of planar waveguides and forming at least one interaction region, wherein said first substrate and said second substrate are located on a same side of said plurality of optical paths.

76. An optical detection device according to claim 75, wherein said first substrate and said second substrate are coupled directly to said plurality of optical paths.

77. An optical detection device according to claim 75, further comprising a housing, wherein said housing is located between said first and second substrates and said plurality of optical paths.

78. A method for the parallel determination of one or more luminescences comprising:

providing at least one light source for emitting detection light, the at least one light source being located on a first substrate;

providing at least one photoelectric detection unit for detecting a light intensity and converting the light intensity into a corresponding electrical signal, the at least one photoelectric detection unit being located on a second substrate;

providing at least one measuring cell for holding a sample to be examined;

using at least one optical path to couple the at least one measuring cell being formed between the at least one light source and the at least one photoelectric detection unit to the at least one light source and the at least one photoelectric detection unit, the at least one light source being a single wavelength surface-emitting semiconductor laser, wherein the at least one optical path comprises a planar waveguide which is coupled to the at least one measuring cell, and wherein the first substrate and the second substrate are located on a same side of the at least one optical path;

providing a sensor layer comprising at least one specific binding partner operable to act as a recognition element for at least one analyte on the at least one planar waveguide, the sensor layer being coupled to the at least one measuring cell and which is selectively sensitive to at least one analyte to be examined in the at least one sample;

bringing the at least one sample into contact with the at least one planar waveguide, coupling excitation light into the at least one planar waveguide, causing the light to pass through the at least one planar waveguide, and thus, exciting in parallel in an evanescent field, at least one luminescent substance in the at least one sample, wherein the at least one luminescent substance is bound to an immobilized specific binding partner acting as a recognition element for the at least one analyte or to another specific binding partner bound to the immobilized specific binding partner on the at least one planar waveguide; and measuring the one or more luminescences produced thereby using photoelectric detection elements.

79. A method according to claim 78, wherein the first substrate and the second substrate are coupled directly to the at least one optical path.

80. A method according to claim 78, wherein a housing is located between the first and second substrates and the at least one optical path.

81. A method for the parallel determination of one or more luminescence, comprising:

providing a plurality of light sources for emitting detection light, the plurality of light sources being located on a first substrate;

providing a corresponding plurality of photoelectric detection units, each associated with a corresponding light source, for detecting a light intensity and converting the light intensity into a corresponding electrical signal, the corresponding plurality of photoelectric detection units being located on a second substrate;

providing at least one measuring cell for holding a sample to be examined;

using a plurality of optical paths each to couple the at least one measuring cell being formed between the light sources and the corresponding photoelectric detection units to the light sources and the corresponding photoelectric detection units, the plurality of light sources comprising at least one linear arrangement of single wavelength edge-emitting semiconductor lasers produced on a common substrate, wherein each of the plurality of optical paths comprises a planar waveguide which is coupled to the at least one measuring cell, and wherein the first substrate and the second substrate are located on a same side of the plurality of optical paths;

providing a sensor layer comprising at least one specific binding partner operable to act as a recognition element for at least one analyte on at least one of the plurality of planar waveguides, the sensor layer being coupled to the at least one measuring cell and being selectively sensitive to at least one analyte to be examined in the at least one sample;

bringing the at least one sample into contact with the plurality of planar waveguides;

coupling excitation light into the plurality of planar waveguides, causing the light to pass through the plurality of planar waveguides, and thus, exciting in parallel in an evanescent field, at least one luminescent substance in the at least one sample wherein, wherein the at least one luminescent substance is bound to an immobilized specific binding partner acting as a recognition element for the at least one analyte or to another specific binding partner bound to the immobilized specific binding partner on at least one of the plurality of planar waveguides; and measuring the one or more luminescences produced thereby using photoelectric detection elements.

82. A method according to claim 81, wherein the first substrate and the second substrate are coupled directly to the plurality of optical paths.

83. An optical detection device according to claim 81, wherein a housing is located between the first and second substrates and the plurality of optical paths.

* * * * *